(12) United States Patent
Dai et al.

(10) Patent No.: US 11,884,679 B2
(45) Date of Patent: Jan. 30, 2024

(54) COMPOUND, DISPLAY PANEL AND DISPLAY APPARATUS

(71) Applicant: Shanghai Tianma AM-OLED Co., Ltd., Shanghai (CN)

(72) Inventors: Wenpeng Dai, Shanghai (CN); Wei Gao, Shanghai (CN); Lei Zhang, Shanghai (CN); Quan Ran, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 586 days.

(21) Appl. No.: 17/128,932

(22) Filed: Dec. 21, 2020

(65) Prior Publication Data

US 2021/0115059 A1     Apr. 22, 2021

(30) Foreign Application Priority Data

Oct. 14, 2020   (CN) .......................... 202011099188.1

(51) Int. Cl.
| | | |
|---|---|---|
| *H01L 51/00* | (2006.01) | |
| *C07D 487/02* | (2006.01) | |
| *C07D 487/14* | (2006.01) | |
| *C07D 471/14* | (2006.01) | |
| *C07D 487/04* | (2006.01) | |

(Continued)

(52) U.S. Cl.
CPC .......... *C07D 487/14* (2013.01); *C07D 471/14* (2013.01); *C07D 487/04* (2013.01); *C07D 487/22* (2013.01); *C07D 491/147* (2013.01); *C07D 495/14* (2013.01); *C07D 495/22* (2013.01); *H10K 85/653* (2023.02); *H10K 85/654* (2023.02); *H10K 85/6565* (2023.02); *H10K 85/6572* (2023.02); *H10K 85/6574* (2023.02); *H10K 85/6576* (2023.02); *H10K 50/11* (2023.02); *H10K 50/156* (2023.02); *H10K 50/18* (2023.02); *H10K 2101/10* (2023.02)

(58) Field of Classification Search
CPC .. C07D 487/14; C07D 471/14; C07D 471/10; C07D 471/20; C07D 471/22; C07D 487/04; C07D 487/22; C07D 491/147; C07D 491/22; C07D 495/14; C07D 495/22; C07D 487/10; C07D 519/00; C07D 487/02; C07D 491/12; H10K 85/653; H10K 85/654; H10K 85/6565; H10K 85/6572; H10K 85/6574; H10K 85/6576; H10K 85/621; H10K 85/40; H10K 85/615; H10K 85/655; H10K 85/656; H10K 85/657; H10K 50/11; H10K 50/156; H10K 50/18; H10K 50/15; H10K 50/17; H10K 2101/10; H10K 50/00; C07F 7/0816; C09K 11/06; C09K 2211/1007; C09K 2211/1011; C09K 2211/1029; C09K 2211/1033; C09K 2211/1037; C09K 2211/1044; C09K 2211/1048; C09K 2211/1051; C09K 2211/1055; C09K 2211/1059; C09K 2211/1062; C09K 2211/1066; C09K 2211/107; C09K 2211/1074; C09K 2211/1088; C09K 2211/1092
USPC ......................................... 540/521; 313/504
See application file for complete search history.

(56) References Cited

FOREIGN PATENT DOCUMENTS

| | | |
|---|---|---|
| JP | 05214334 A | 1/1992 |
| JP | 04020031 A | 8/1993 |

*Primary Examiner* — Charanjit Aulakh
(74) *Attorney, Agent, or Firm* — TAROLLI, SUNDHEIM, COVELL & TUMMINO L.L.P.

(57) ABSTRACT

Provided is a compound including a moiety A and one or two moieties B fused with the moiety A at fusing sites, in which X is N, O, S or C; and when X is O or S, $Ar_2$-$L_1$- is absent; $Y_1$-$Y_4$ are each independently C or N; $L_1$ and $L_2$ are each independently a single bond, a substituted or unsubstituted C6-C30 arylene, a substituted or unsubstituted C10-C40 fused arylene, or a substituted or unsubstituted C4-C30 heteroarylene; $Ar_1$ and $Ar_2$ are each independently a substituted or unsubstituted C6-C30 aryl, a substituted or unsubstituted C10-C40 fused aryl, a substituted or unsubstituted C4-C30 heteroaryl, or a substituted or unsubstituted C6-C40 fused heteroaryl, and * represents one of the fusing sites, N or $CR_a$, where $R_a$ is a substituted or unsubstituted C1-C20 alkyl, a substituted or unsubstituted C6-C30 aryl, or a substituted or unsubstituted C3-C30 heteroaryl.

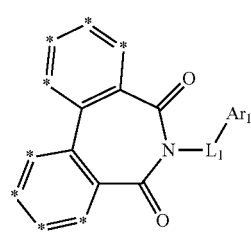

A

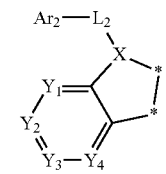

B

7 Claims, 2 Drawing Sheets

(51) Int. Cl.
_C07D 487/22_ (2006.01)
_C07D 491/147_ (2006.01)
_C07D 495/14_ (2006.01)
_C07D 495/22_ (2006.01)
_H10K 85/60_ (2023.01)
_H10K 50/11_ (2023.01)
_H10K 50/18_ (2023.01)
_H10K 50/15_ (2023.01)
_H10K 101/10_ (2023.01)

COMPOUND, DISPLAY PANEL AND DISPLAY APPARATUS

CROSS-REFERENCE TO RELATED APPLICATIONS

The present application claims priority to Chinese Patent Application No. 202011099188.0, filed on Oct. 14, 2020, the content of which is incorporated herein by reference in its entirety.

TECHNICAL FIELD

The present application disclosure relates to the technical field of electroluminescent materials, and particularly, to a compound having an imide structure, and a display panel and a display apparatus containing the compound.

BACKGROUND

As a new generation of display technology, organic electroluminescent materials, such as organic light-emitting diodes (OLED), have been widely used in flat-panel displays, flexible displays, solid-state lighting and vehicle displays, due to their advantageous ultra-thinness, self-luminescence, wide viewing angle, fast response, high luminous efficiency, good temperature adaptability, simple manufacturing process, low driving voltage, low energy consumption and the like.

Depending upon the luminescence mechanisms, the light emitted by OLEDs can be classified into electrofluorescence and electrophosphorescence. Fluorescence is the light emitted during a radiation attenuation transition of singlet excitons, and phosphorescence is light emitted during attenuation transition of triplet excitons to the ground state. According to the spin-statistics theorem, a probability ratio of forming singlet excitons to forming triplet excitons is 1:3. The electrofluorescent materials have an internal quantum efficiency of no more than 25%, and an external quantum efficiency of generally less than 5%. Theoretically, the electrophosphorescent materials have an internal quantum efficiency of up to 100%, and an external quantum efficiency of up to 20%. In 1998, both Professor Ma Yuguang from Jilin University in China and Professor Forrest from Princeton University in the United States reported that a phenomenon of electrophosphorescence was obtained and explained by doping ruthenium complexes and platinum complexes as dyes into the light-emitting layer, and pioneered the application of the prepared phosphorescent materials to electroluminescent devices.

The long lifetime (μs) of phosphorescent heavy metal materials may lead to triplet state-triplet state quenching and concentration quenching at high current densities and result in a degradation of device performance. Therefore, phosphorescent heavy metal materials are usually doped into suitable host materials to form a host-guest doped system. In this way, energy transfer is optimized, and luminous efficiency and lifetime are maximized. At present, heavy metal doping materials have been commercialized, and development of alternative doping materials has been proven challenging. Thus, it is a new trend to develop the phosphorescent host materials. For achieving better performances of the OLED devices, it is urgent to develop an outstanding light-emitting host material for OLEDs.

SUMMARY

In view of the above, the present disclosure provides a compound, including a moiety A and one or two moieties B fused with the moiety A at fusing sites,

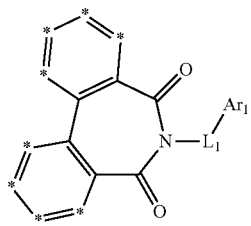

A

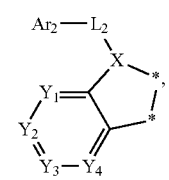

B wherein X is a nitrogen atom, an oxygen atom, a sulfur atom or a carbon atom; when X is an oxygen atom or a sulfur atom, $Ar_2$-$L_2$- is absent; and when X is a nitrogen atom or a carbon atom, $Ar_2$-$L_2$- is present;

$Y_1$-$Y_4$ are each independently a carbon atom or a nitrogen atom;

$L_1$ and $L_2$ are each independently selected from the group consisting of a single bond, a substituted or unsubstituted C6-C30 arylene, a substituted or unsubstituted C10-C40 fused arylene, and a substituted or unsubstituted C4-C30 heteroarylene;

$Ar_1$ and $Ar_2$ are each independently selected from the group consisting of a substituted or unsubstituted C6-C30 aryl, a substituted or unsubstituted C10-C40 fused aryl, a substituted or unsubstituted C4-C30 heteroaryl, and a substituted or unsubstituted C6-C40 fused heteroaryl; and each * represents one of the fusing sites, a nitrogen atom, or $CR_a$, wherein $R_a$ is selected from the group consisting of a substituted or unsubstituted C1-C20 alkyl, a substituted or unsubstituted C6-C30 aryl, and a substituted or unsubstituted C3-C30 heteroaryl.

The compound of the present disclosure contains a seven-membered nitrogen heterocyclic ring, and has high hole and electron mobility and high thermal stability. An OLED device prepared with the compound has high device efficiency, lower turn-on voltage and long service life.

DESCRIPTION OF EMBODIMENTS

Figure 1:
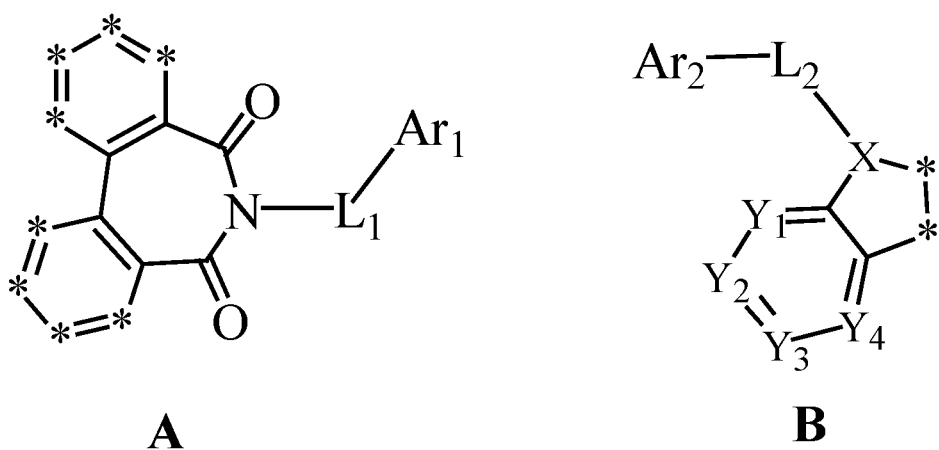
FIG. 1 is a general formula of a compound according to the present disclosure.
Figure 2:
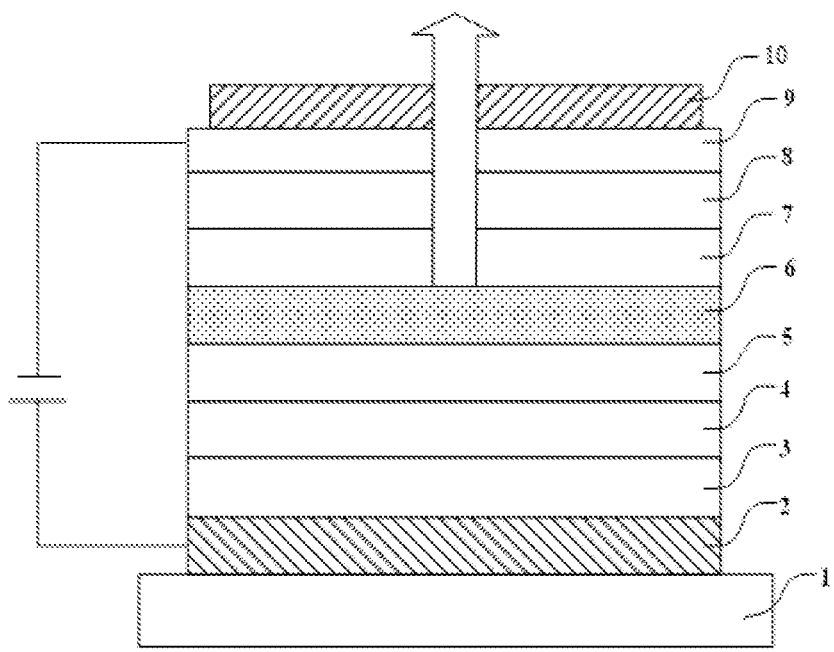
FIG. 2 is a schematic diagram of an OLED device according to an embodiment of the present disclosure.

The present disclosure will be further described below with reference to embodiments and comparative examples. It should be understood that the present disclosure is not limited the following embodiments. Without departing from the scope of the technical solutions of the present disclosure, any modifications or equivalent substitutions to the technical solutions of the present disclosure shall fall within the protection scope of the present disclosure.

The present disclosure provides a compound, including a moiety A and one or two moieties B fused with the moiety A at fusing sites,

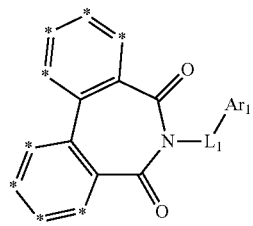

A

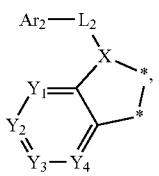

B wherein X is a nitrogen atom, an oxygen atom, a sulfur atom or a carbon atom; when X is an oxygen atom or a sulfur atom, $Ar_2$-$L_2$- is absent; and when X is a nitrogen atom or a carbon atom, $Ar_2$-$L_2$- is present;

$Y_1$-$Y_4$ are each independently a carbon atom or a nitrogen atom;

$L_1$ and $L_2$ are each independently selected from the group consisting of a single bond, a substituted or unsubstituted C6-C30 arylene, a substituted or unsubstituted C10-C40 fused arylene, and a substituted or unsubstituted C4-C30 heteroarylene;

$Ar_1$ and $Ar_2$ are each independently selected from the group consisting of a substituted or unsubstituted C6-C30 aryl, a substituted or unsubstituted C10-C40 fused aryl, a substituted or unsubstituted C4-C30 heteroaryl, and a substituted or unsubstituted C6-C40 fused heteroaryl; and each * represents one of the fusing sites, a nitrogen atom, or $CR_a$, wherein $R_a$ is selected from the group consisting of a substituted or unsubstituted C1-C20 alkyl, a substituted or unsubstituted C6-C30 aryl, and a substituted or unsubstituted C3-C30 heteroaryl.

In the compound according to the present disclosure, the C4-C30 heteroarylene can be C4-C10 heteroarylene or C5-C20 heteroarylene; and the C4-C30 heteroaryl can be C4-C10 heteroaryl or C4-C20 heteroaryl.

In the compound according to the present disclosure, the seven-membered ring (A ring) containing an imide structure is fused with B to change a planarity of the entire molecule, increasing a distortion of the molecular structure. In this way, the molecules are unlikely to aggregate, and the generated excitons are unlikely to be quenched, thereby ultimately improving the efficiency of the OLED devices using the compound.

In an embodiment of the compound according to the present disclosure, the compound has a structure represented by any one of formula 1-1 to formula 1-12, formula 1-1

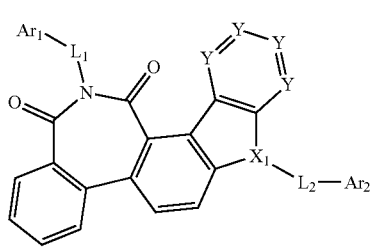

formula 1-2

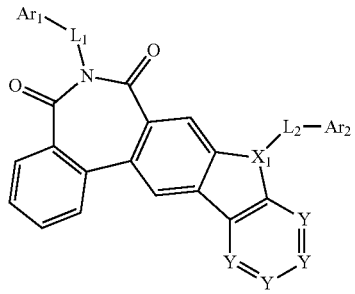

formula 1-3

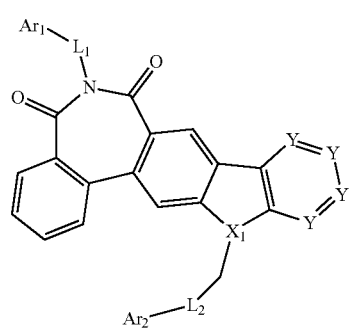

formula 1-4

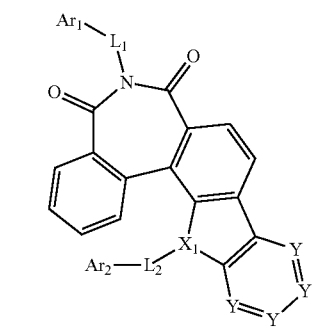

formula 1-5

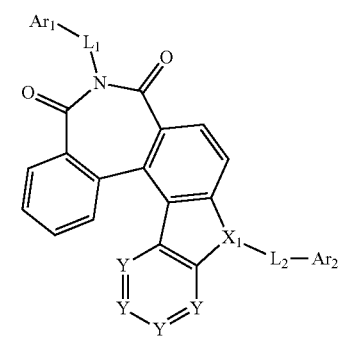

formula 1-6

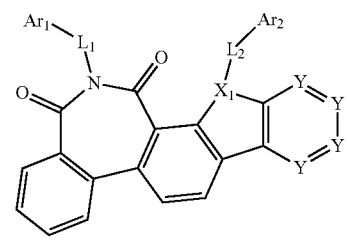

formula 1-7

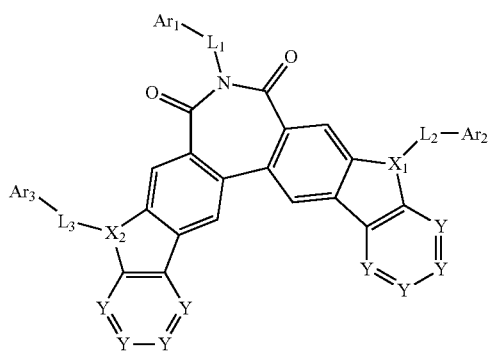

formula 1-8

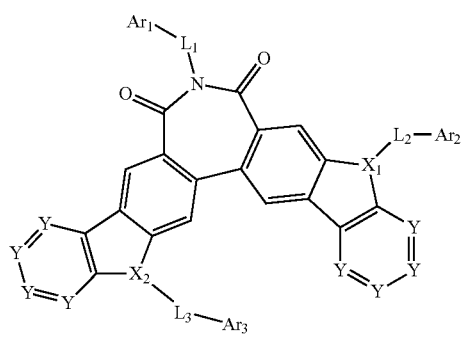

formula 1-9

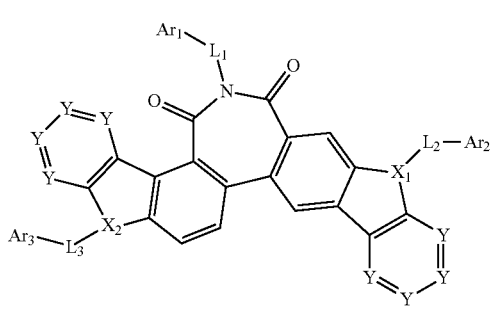

formula 1-10

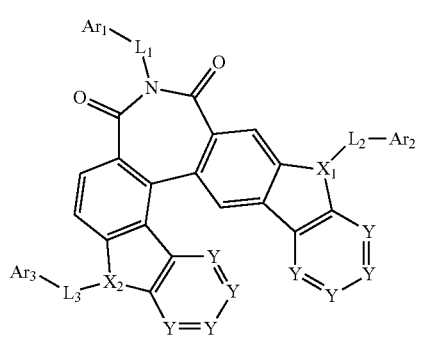

formula 1-11

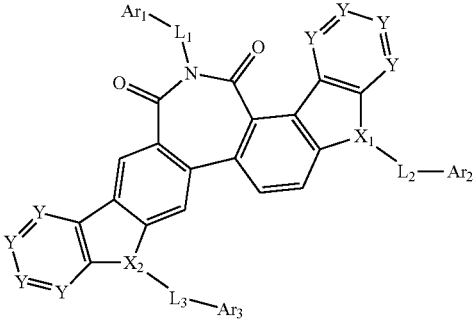

formula 1-12

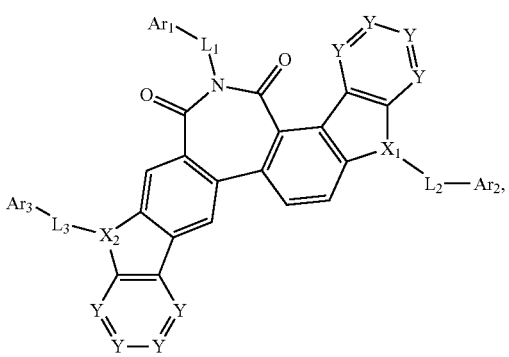

wherein $L_3$ is selected from the group consisting of a single bond, a substituted or unsubstituted C6-C30 arylene, a substituted or unsubstituted C12-C40 fused arylene, and C5-C30 heteroarylene.

In an embodiment of the compound according to the present disclosure, the one or two moieties B is fused with the moiety A, and X is an oxygen atom or a sulfur atom. The seven-membered ring (A ring) containing the imide structure is fused with B to change the planarity of the entire molecule, increasing the distortion of the molecular structure. In this way, the molecules are unlikely to aggregate, and the generated excitons are unlikely to be quenched, thereby ultimately improving the efficiency of the OLED device using the compound. The moiety B can be fused with moiety A to form dibenzopyrrolyl(carbazolyl), dibenzofuryl, dibenzothienyl or other groups, which can change the planarity of the entire molecule, thereby improving device efficiency.

In an embodiment of the compound according to the present disclosure, the one or two moieties B are two moieties B, that is, two moieties B are fused with the moiety A, and at least one X of the two moieties B is a nitrogen atom.

In an embodiment of the compound according to the present disclosure, one or two of $Y_1$-$Y_4$ are a nitrogen atom.

HOMO energy level, as well as LUMO energy level of the molecules can be adjusted in a certain extent by increasing the number of nitrogen atoms in structure B. In this way, when the molecules are used as a light-emitting host material, an energy level difference between the light-emitting host material and a hole transmission material around the light-emitting host material, avoiding the formation of exciplexes that damages the hole transmission material in the device using the compound and reduces the service life of the device.

In an embodiment of the compound according to the present disclosure, $L_1$ and $L_2$ are each independently a group represented by any one of formula 2-1 to formula 2-20:

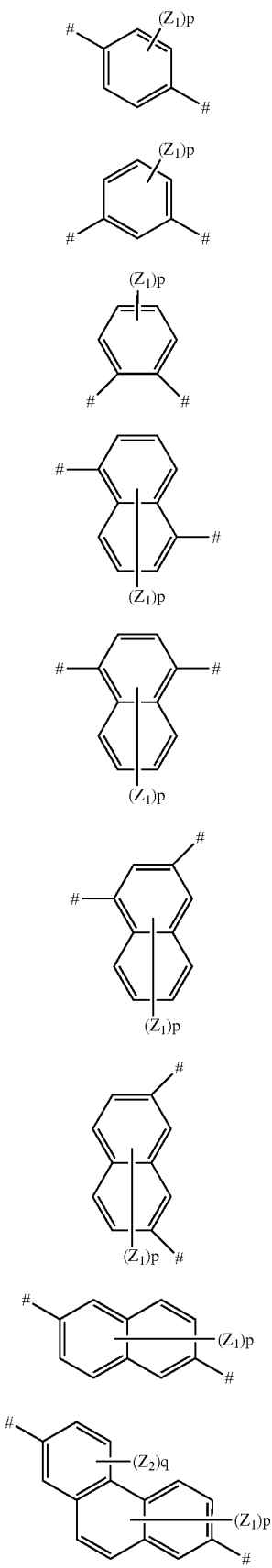
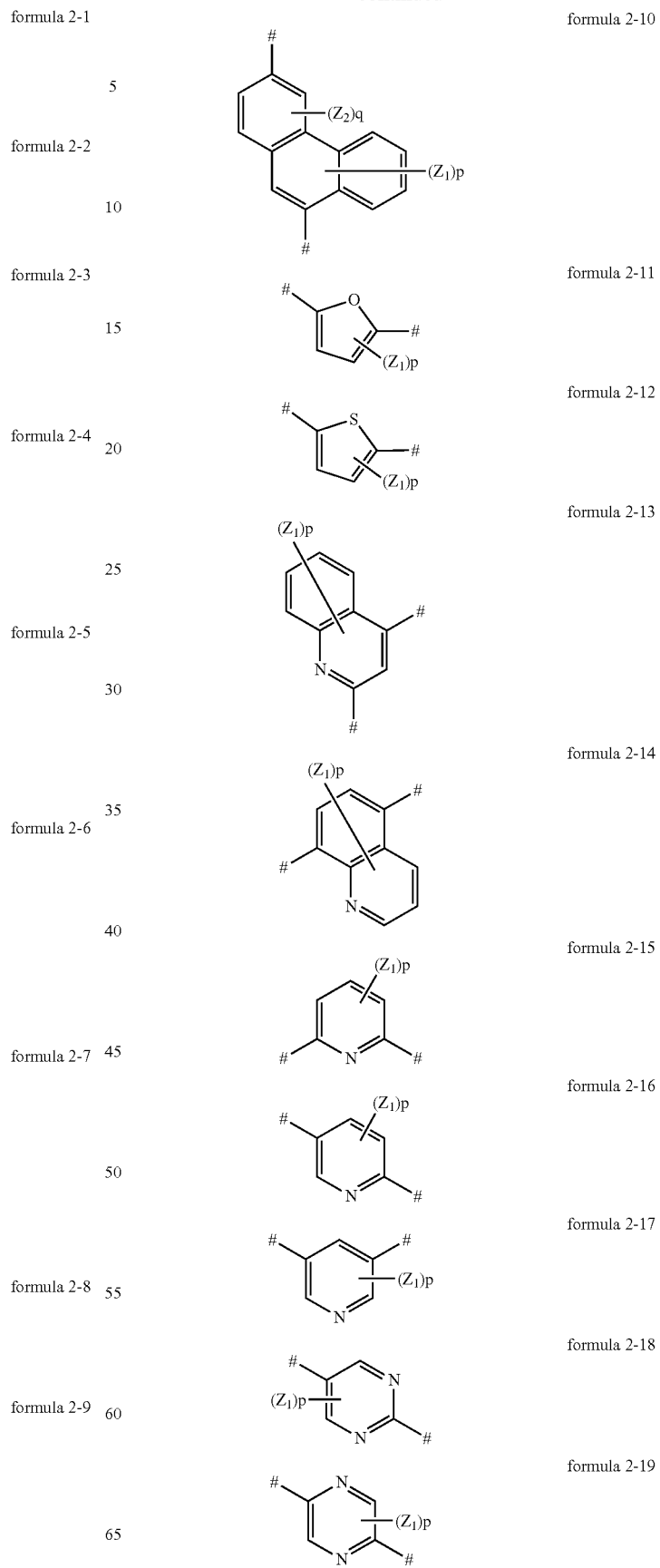

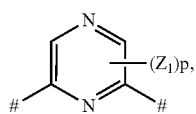

formula 2-20 in which $Z_1$ and $Z_2$ are each independently selected from the group consisting of a hydrogen atom, a substituted or unsubstituted C6-C30 aryl, a substituted or unsubstituted C6-C30 fused aryl, a substituted or unsubstituted C6-C30 fused heteroaryl, a substituted or unsubstituted C1-C16 alkyl, and a substituted or unsubstituted C1-C16 alkoxy;

p and q are each independently 1, 2 or 3; and

\# represents a bonding position.

In an embodiment of the compound according to the present disclosure, $L_1$ and $L_2$ are each independently a group represented by any one of formula 3-1 to formula 3-16:

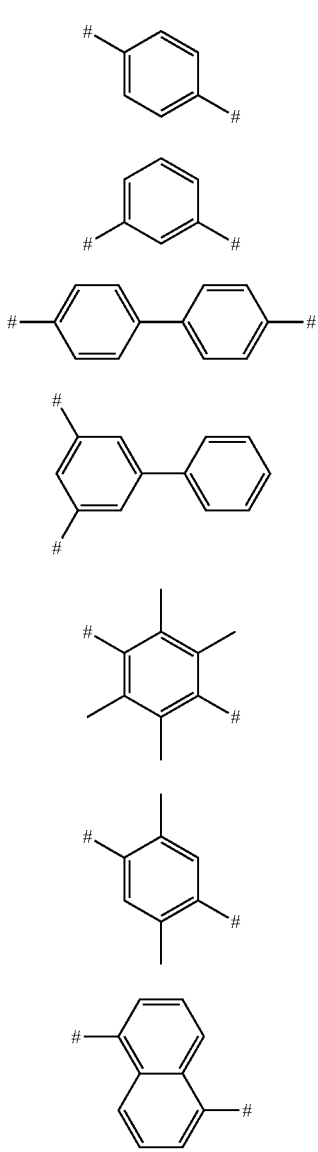

formula 3-1 formula 3-2 formula 3-3 formula 3-4 formula 3-5 formula 3-6 formula 3-7

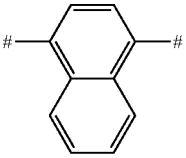

formula 3-8

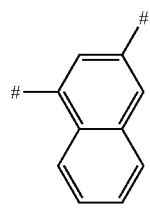

formula 3-9

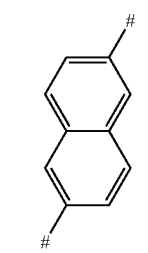

formula 3-10

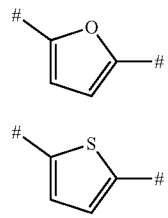

formula 3-11

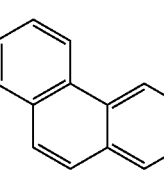

formula 3-12

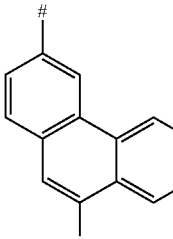

formula 3-13

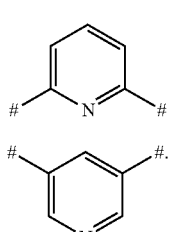

formula 3-14

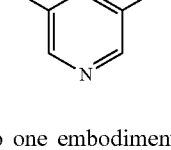

formula 3-15

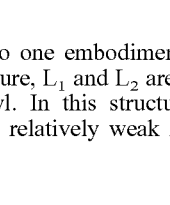

formula 3-16

According to one embodiment of the compound of the present disclosure, $L_1$ and $L_2$ are single bonds, and $Ar_1$ and $Ar_2$ are phenyl. In this structure, on the one hand, the compound has relatively weak molecular conjugate and a high triplet energy level, and the emitted color is blue-shifted, and the compound can be used as a blue-light emitting material; and on the other hand, the compound has a small molecular weight, low sublimation temperature, and good thermal stability.

In an embodiment of the compound according to the present disclosure, the compound is any one of the following compounds:

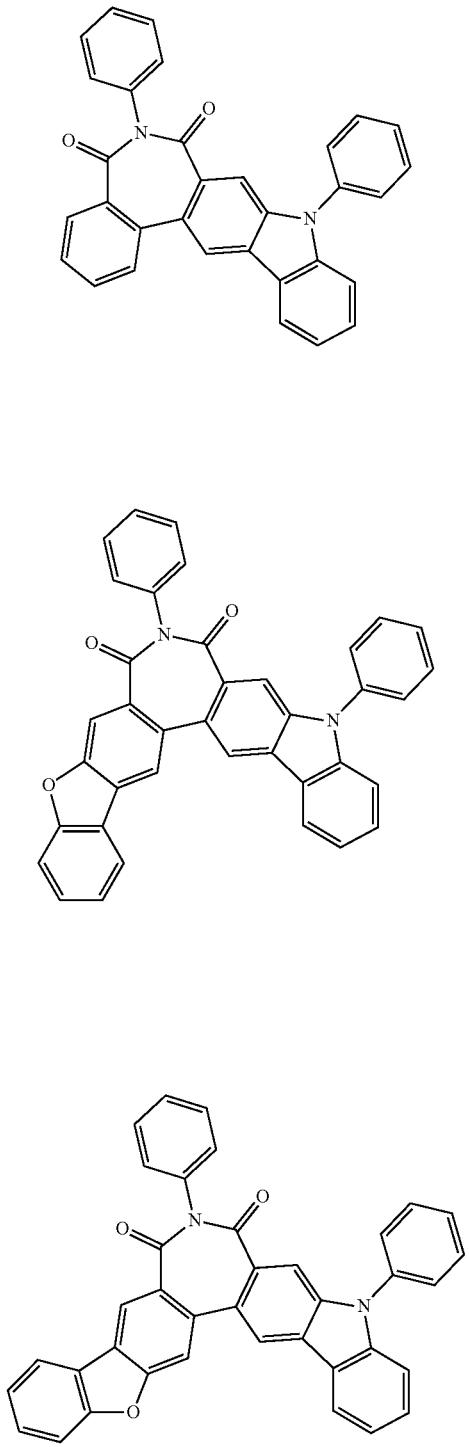

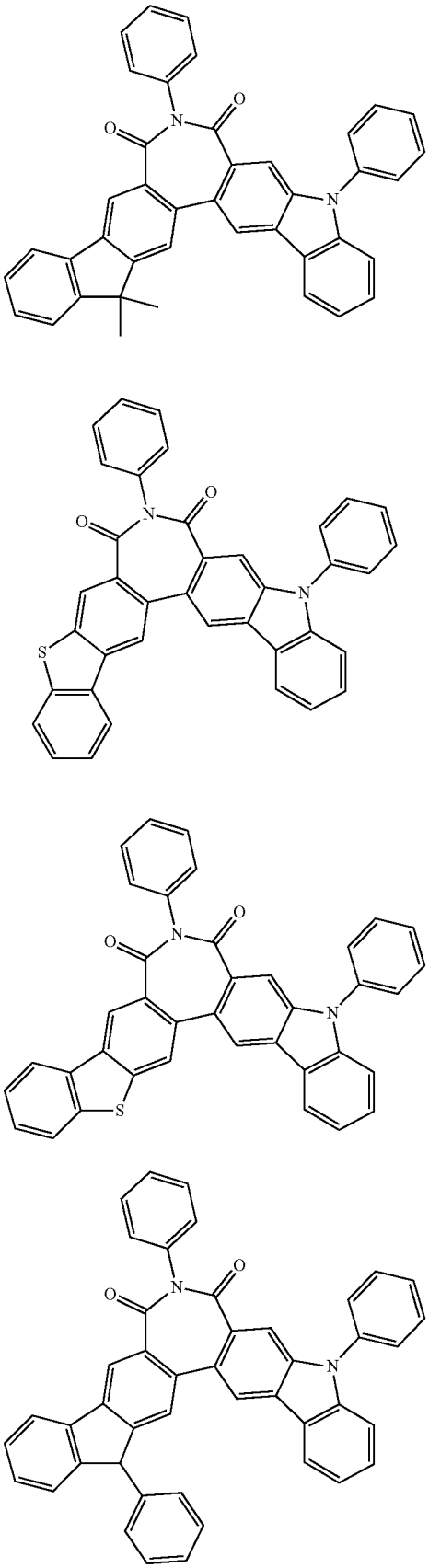

P8
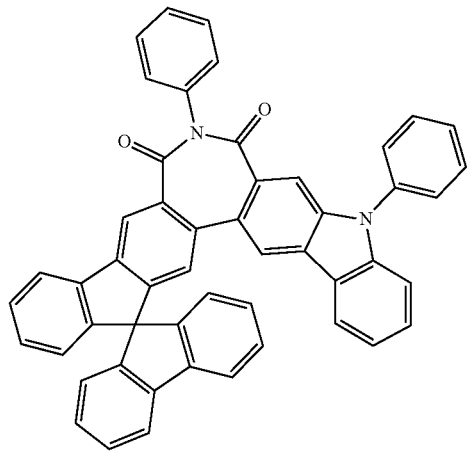
P9
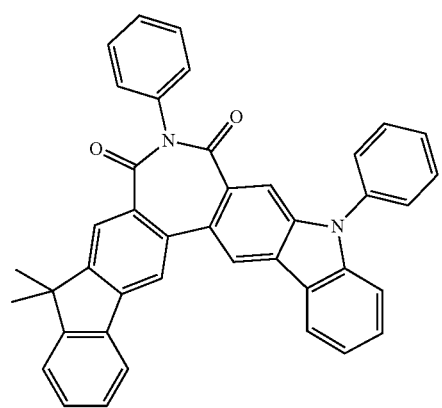
P10
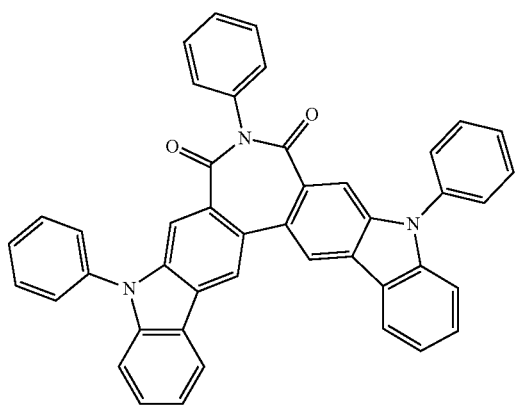
P11
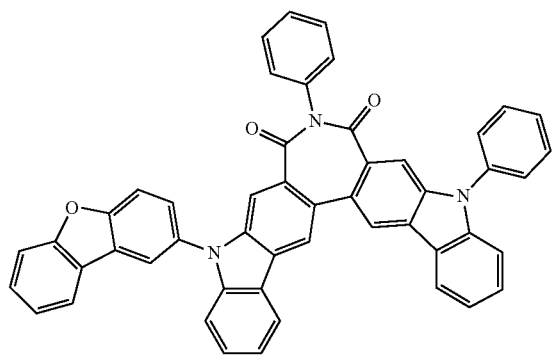
P12
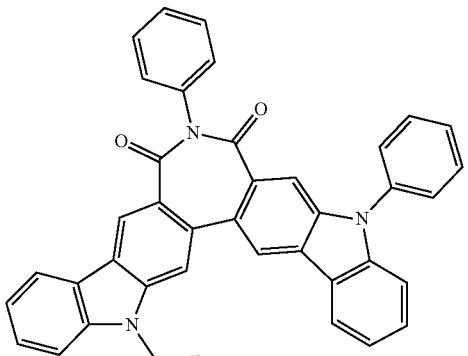
P13
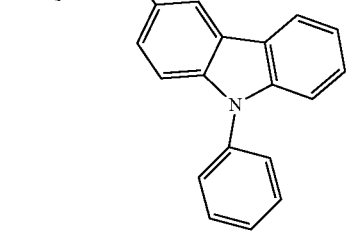
P14
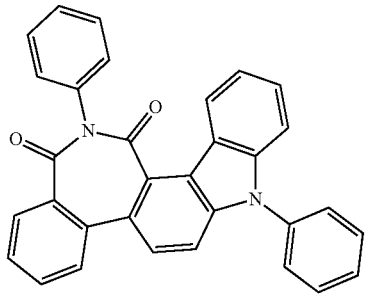
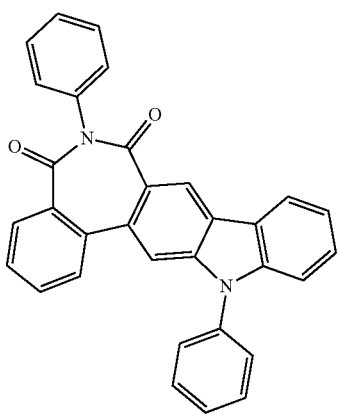

P15
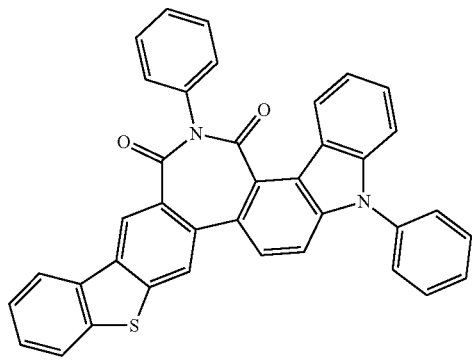
P16
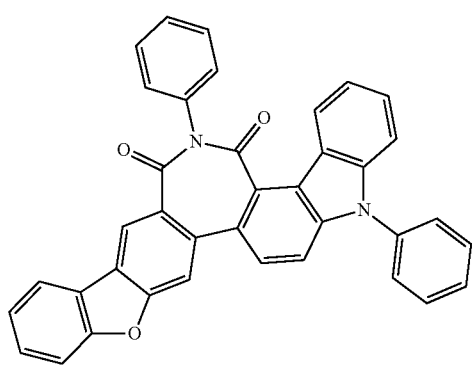
P17
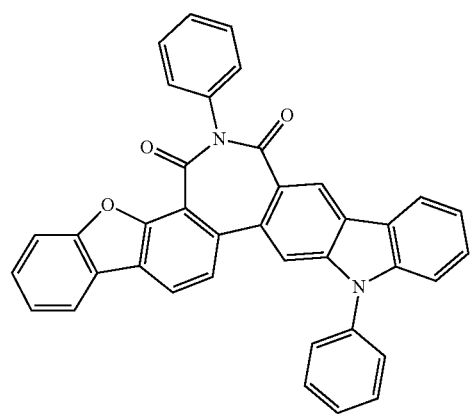
P18
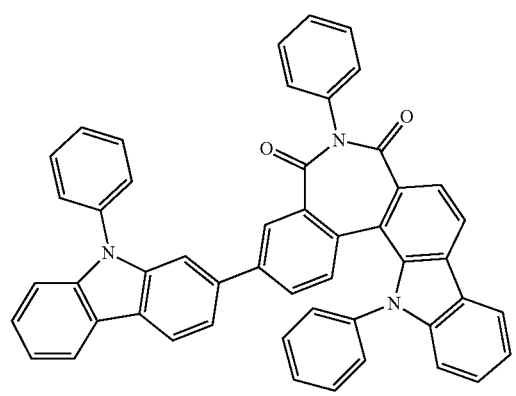
P19
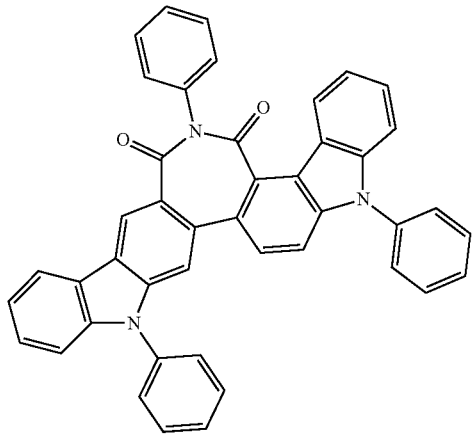
P20
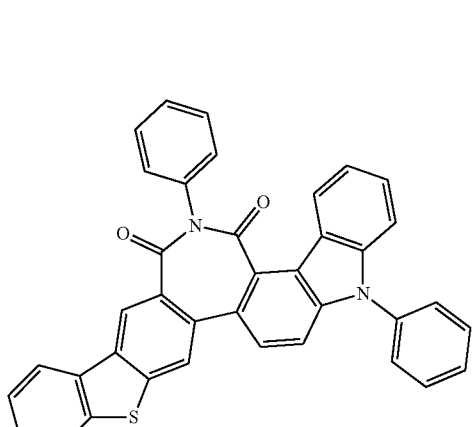
P21
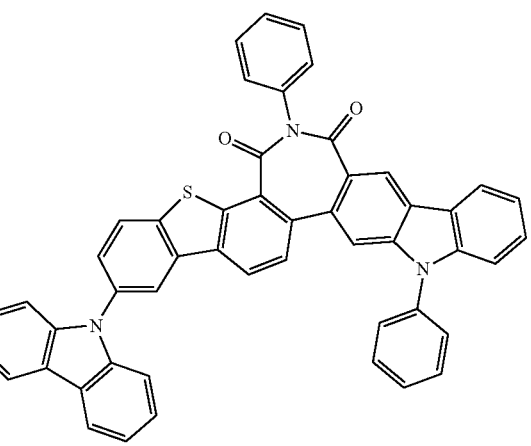

P22
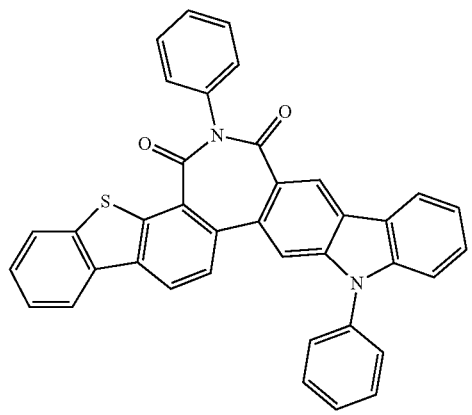
P23
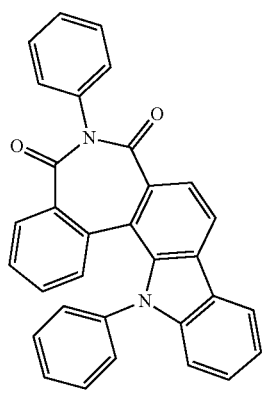
P24
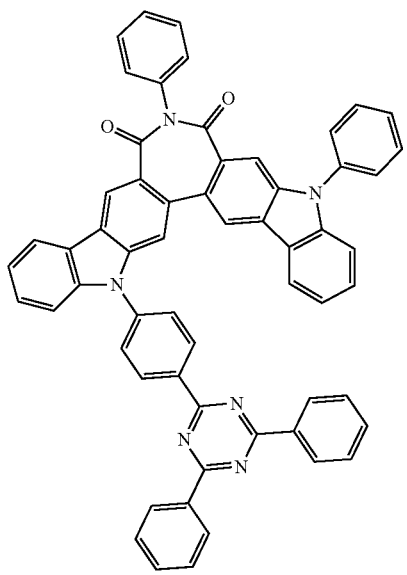
P25
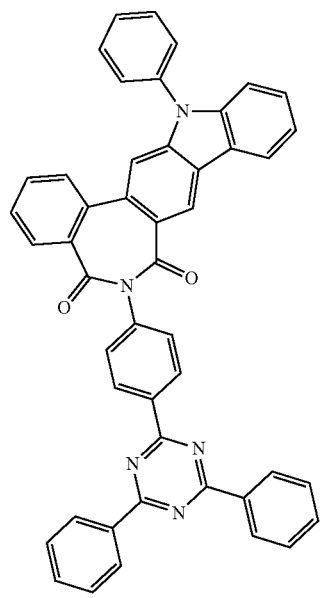
P26
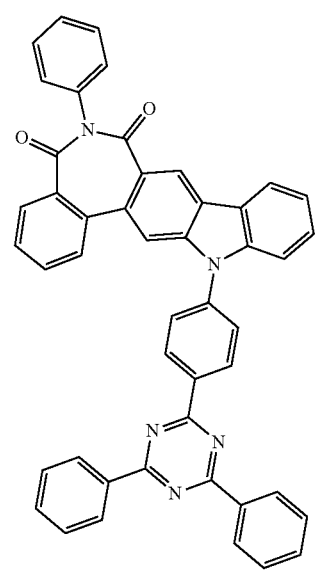

P27
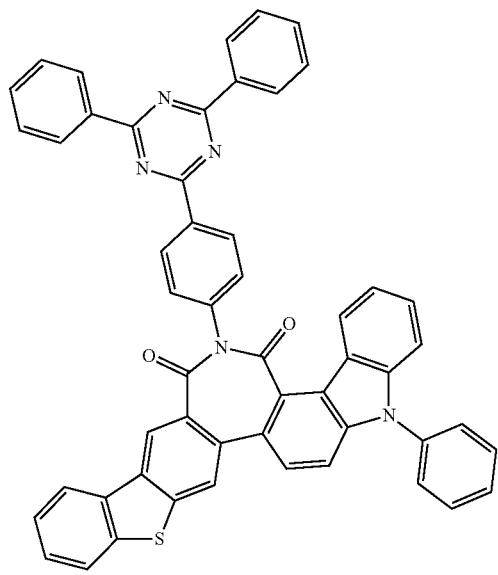
P28
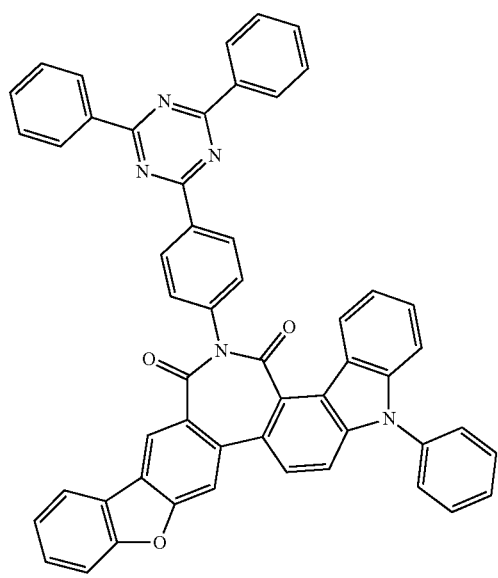
P29
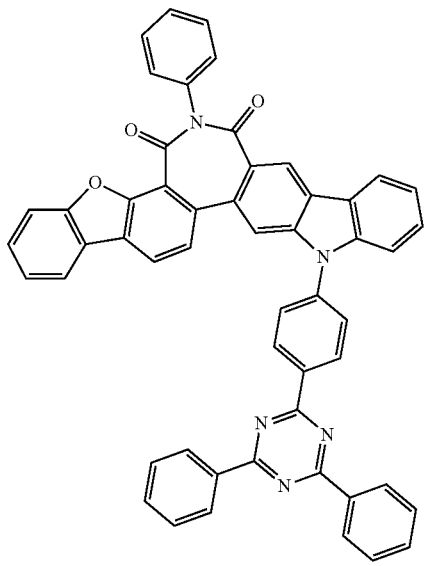
P30
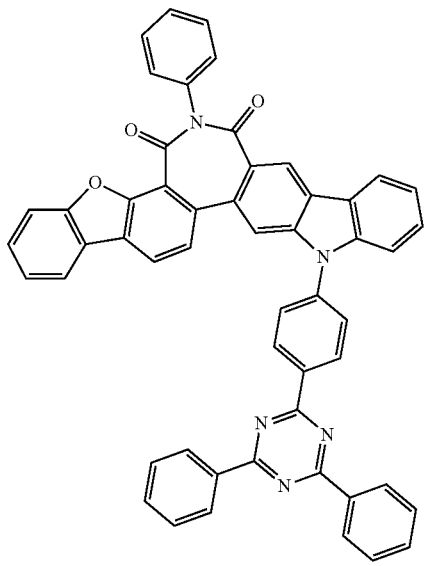
P31
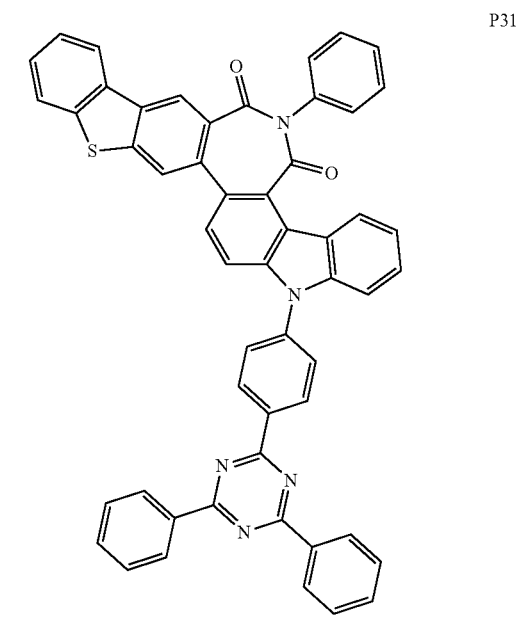
P32
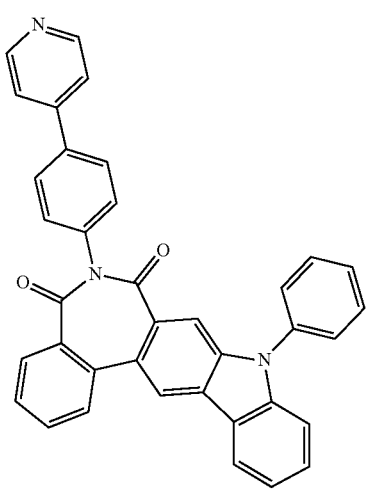

P33
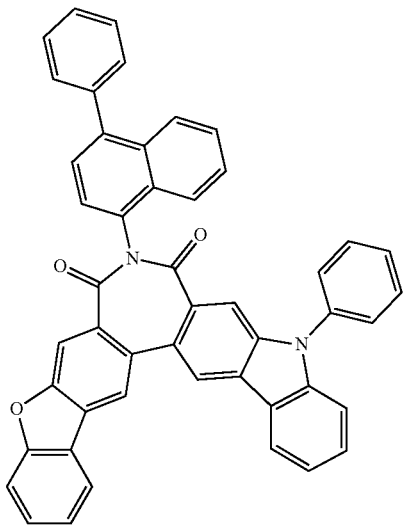
P34
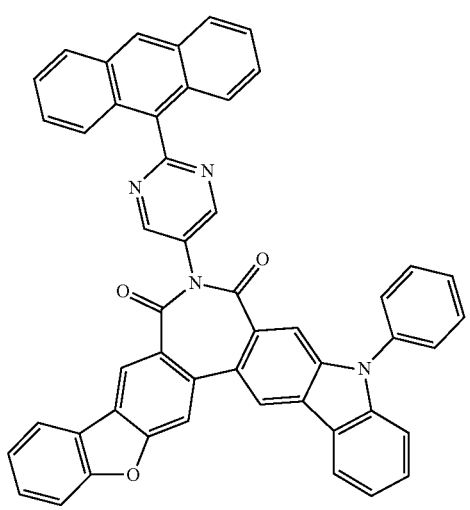
P35
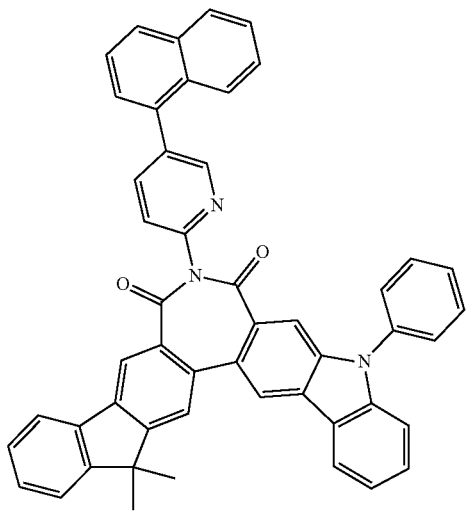
P36
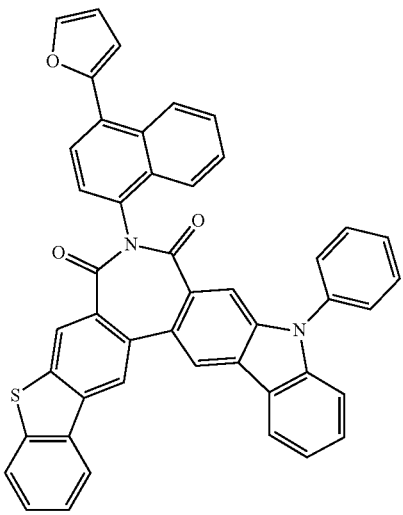
P37
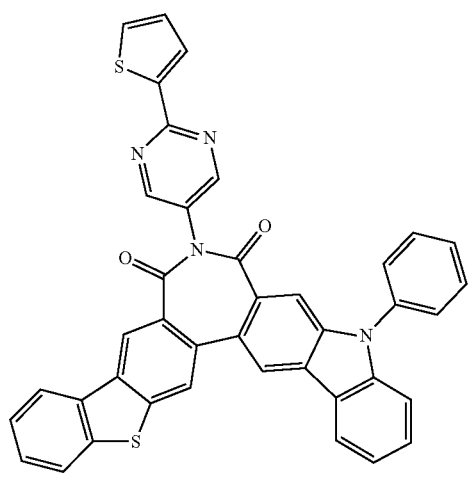
P38
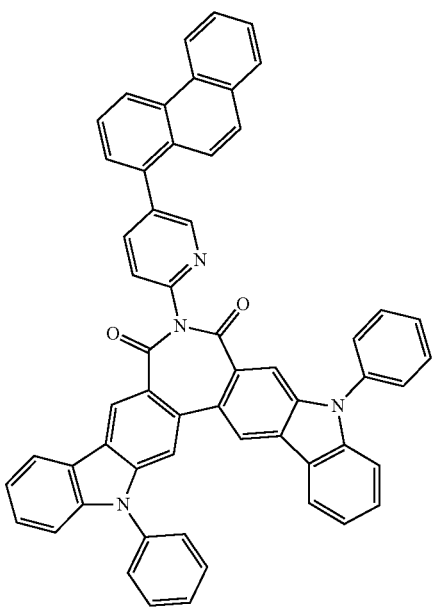

P39
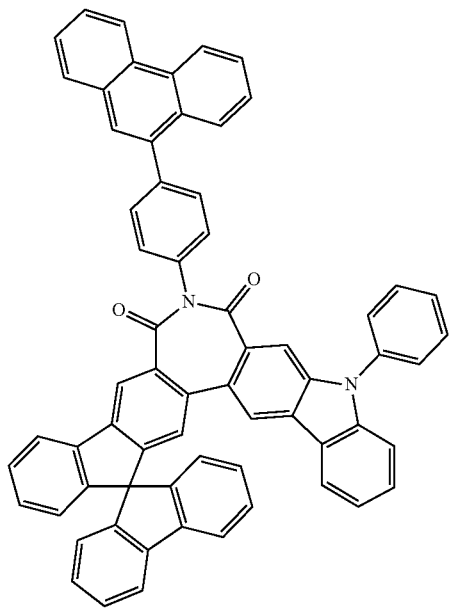
P40
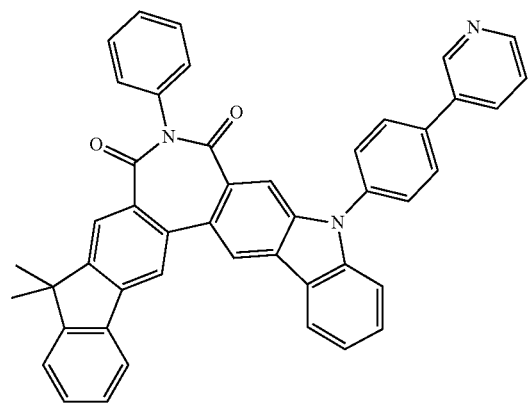
P41
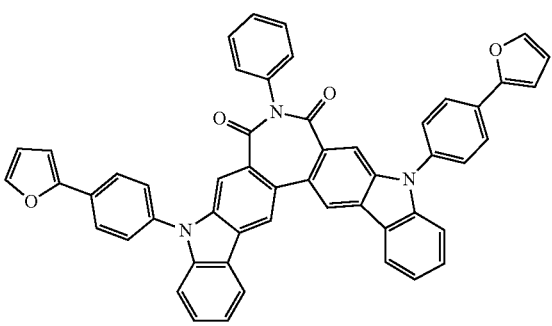
P42
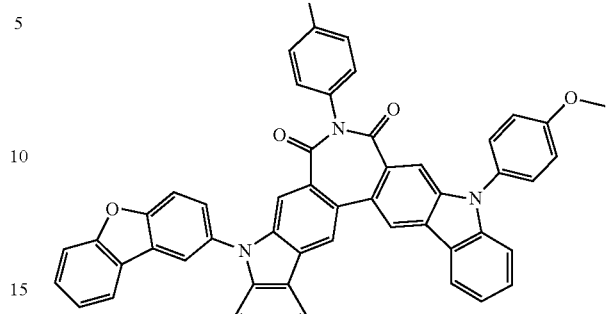
P43
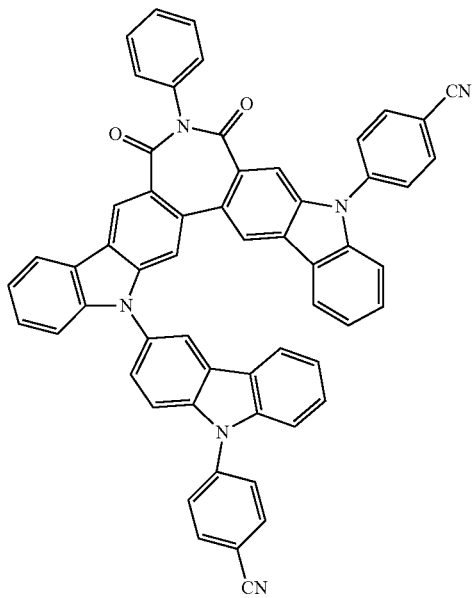
P44
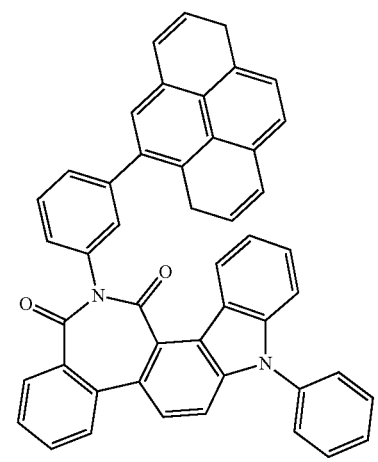

P45
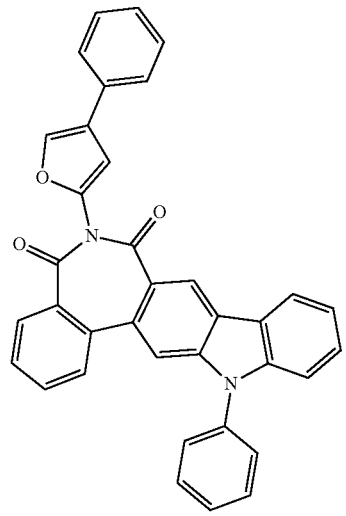
P46
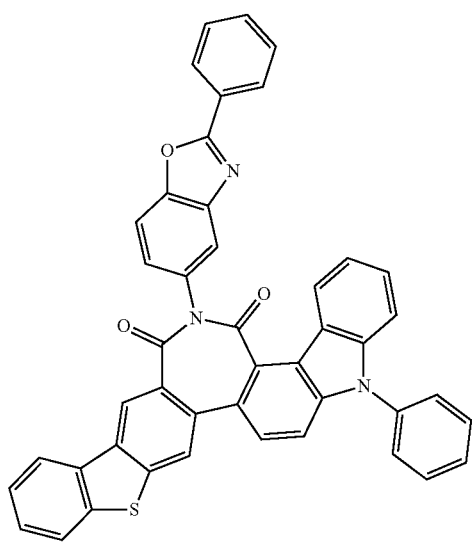
P47
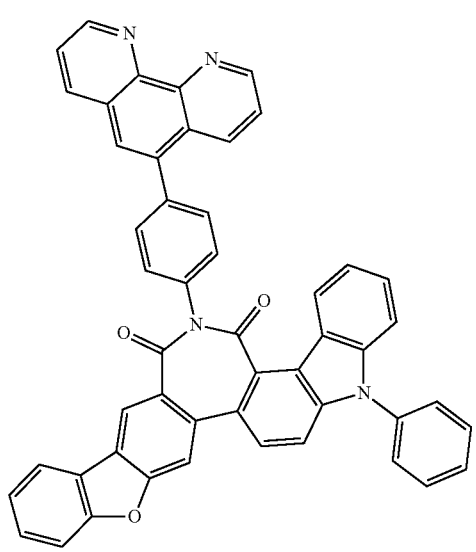
P48
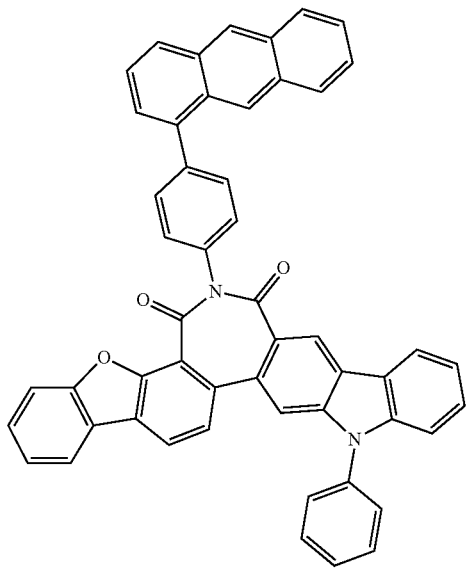
P49
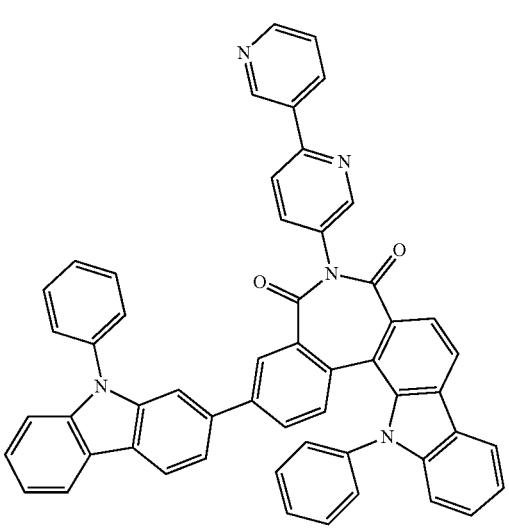
P50
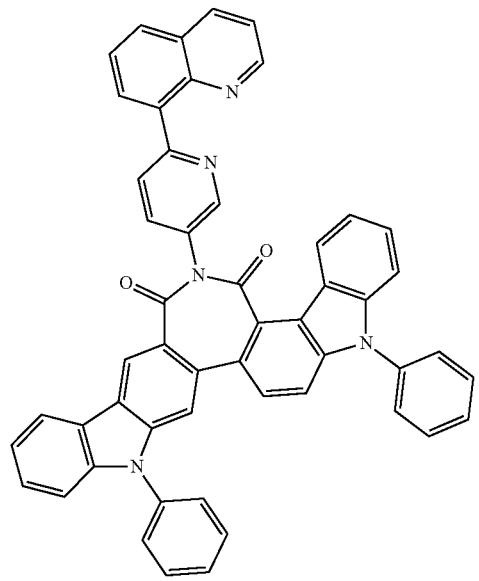

P51
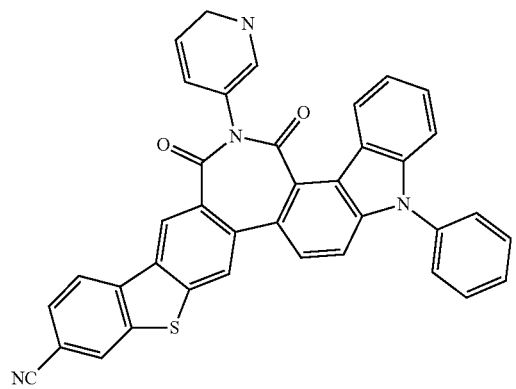
P52
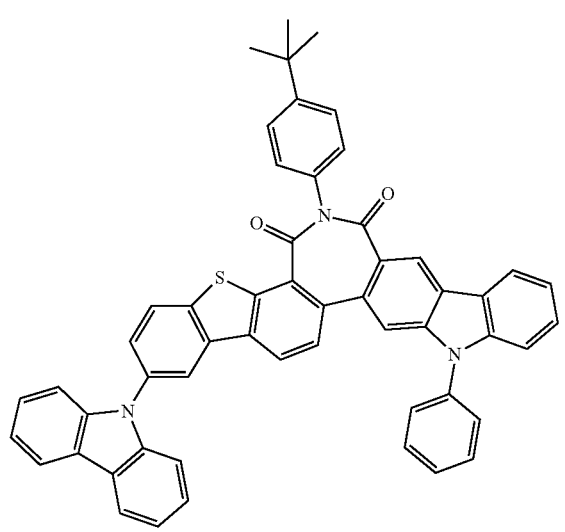
P53
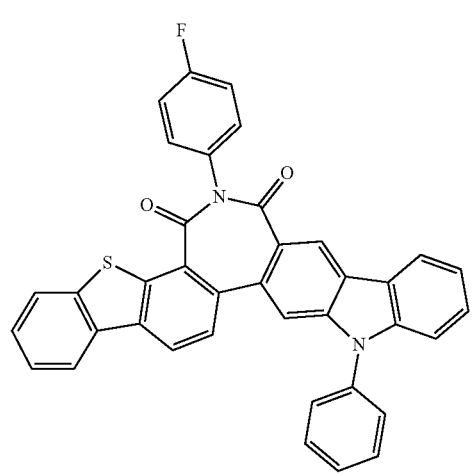
P54
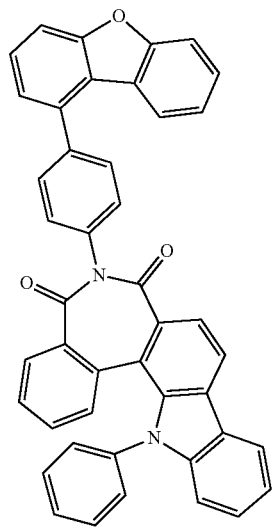
P55
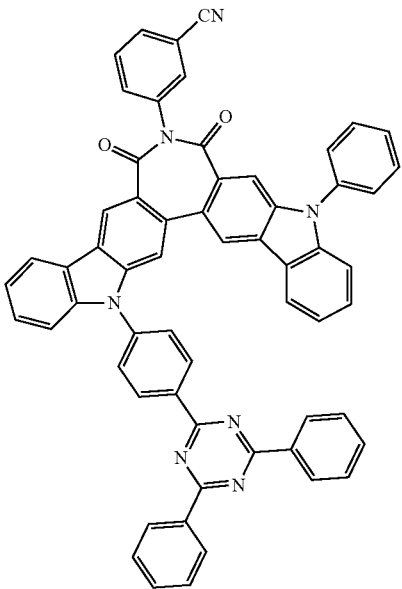

P56
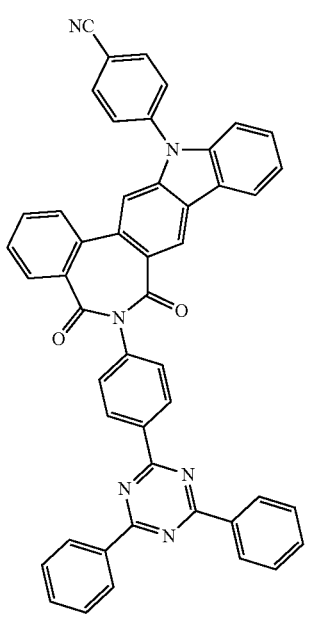
P58
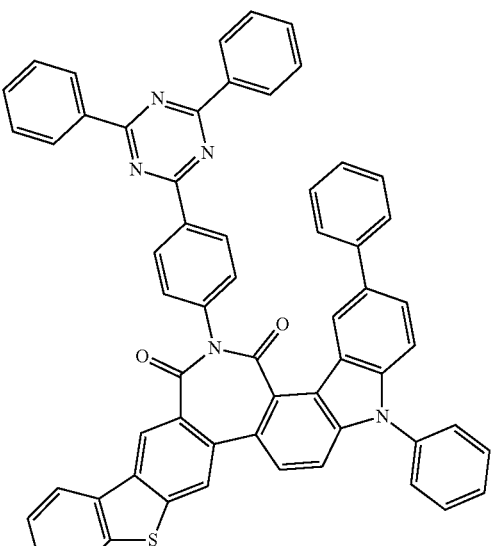
P57
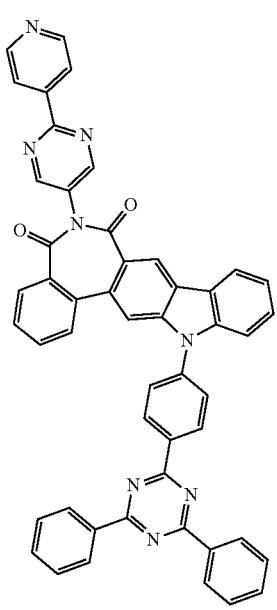
P59
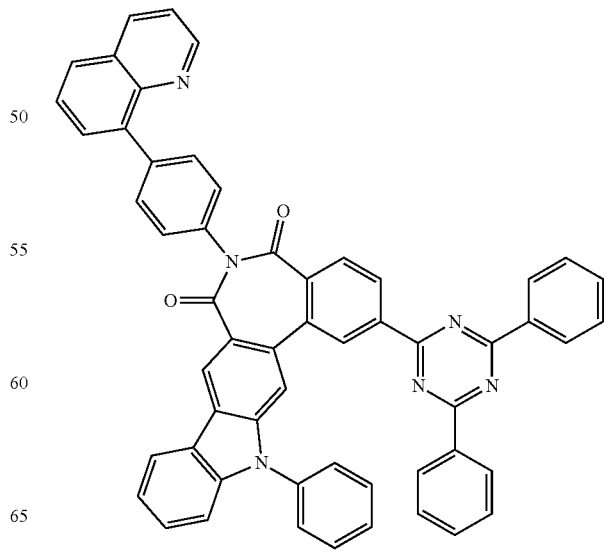

31
-continued
P60
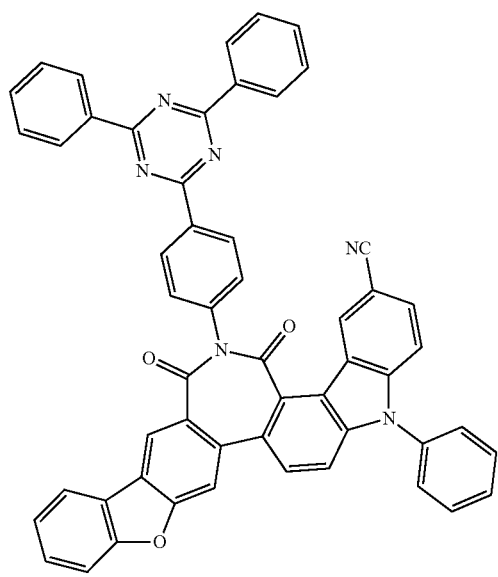
32
-continued
P62
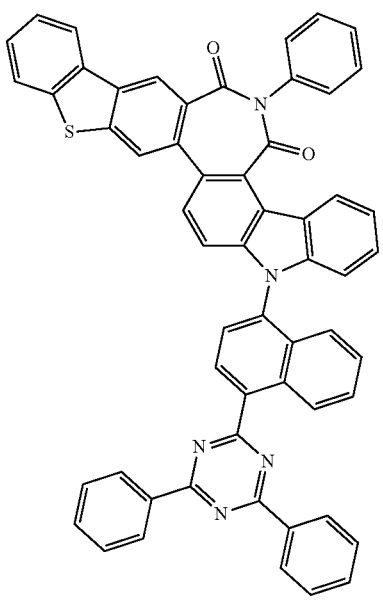
P63
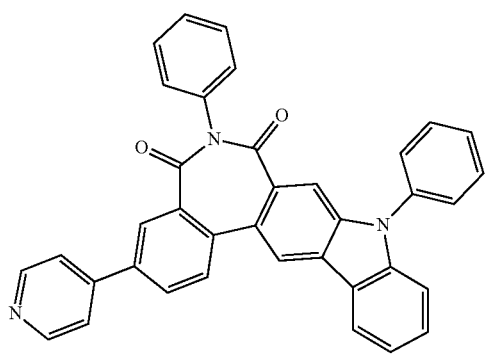
P61
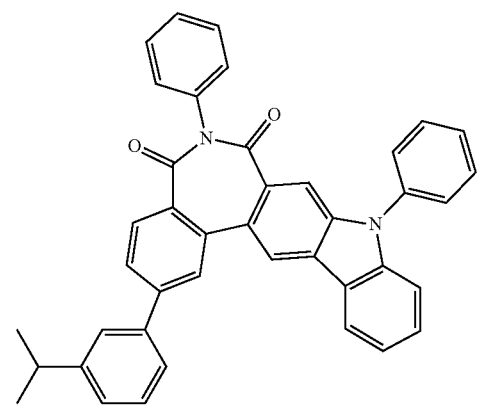
P64

-continued
P65
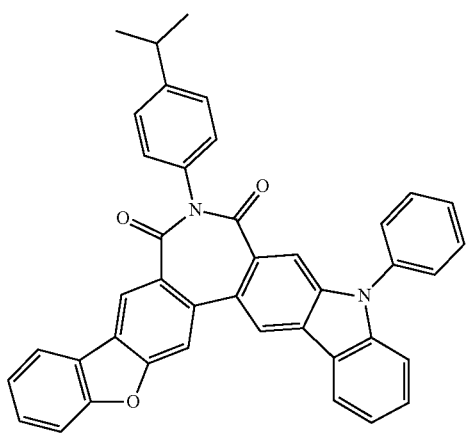
P66
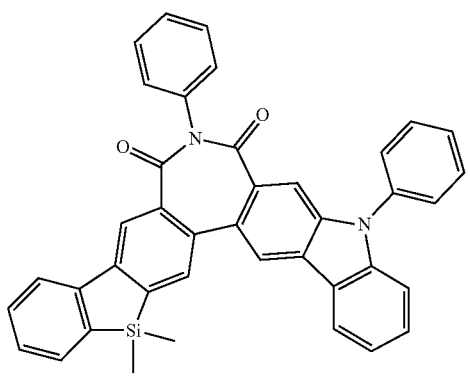
P67
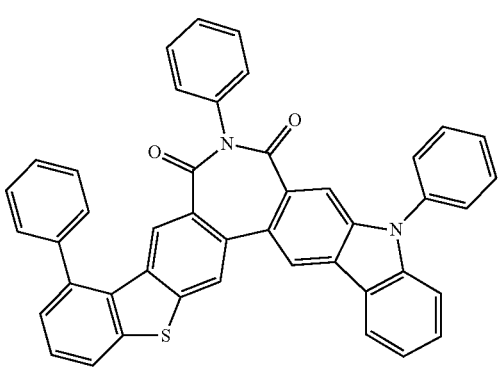
-continued
P69
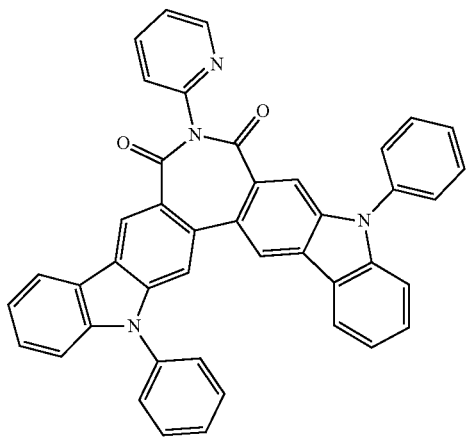
P70
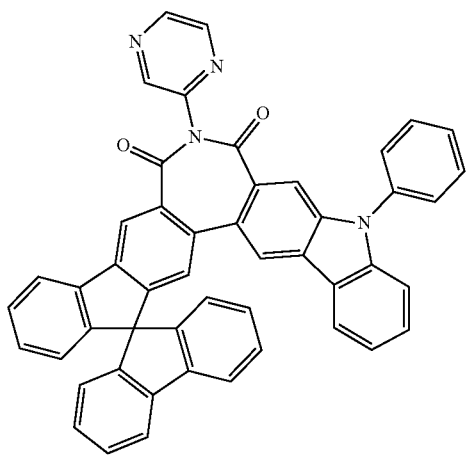
P71
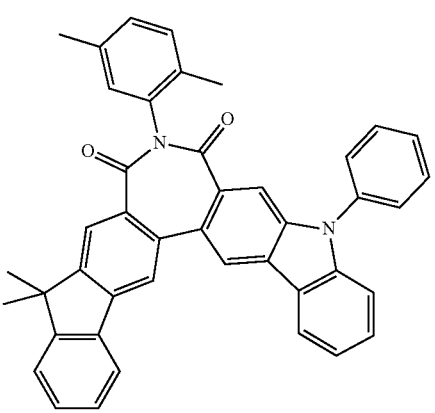

P72
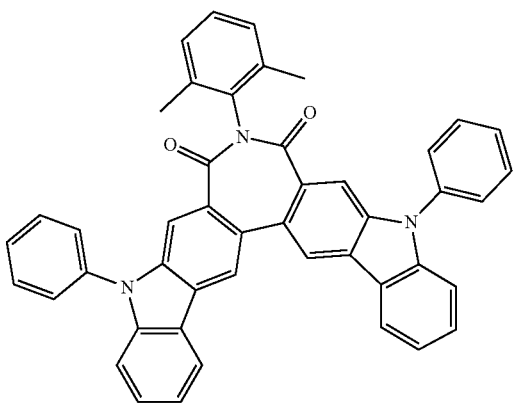
P73
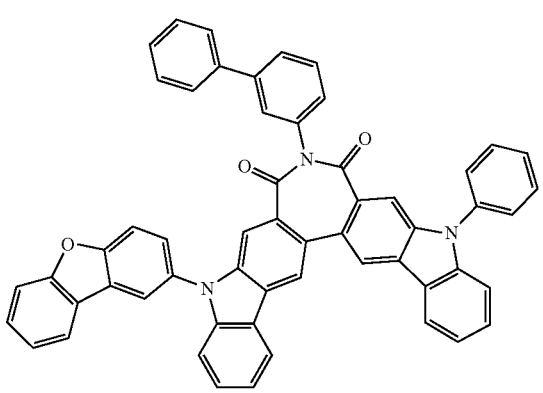
P74
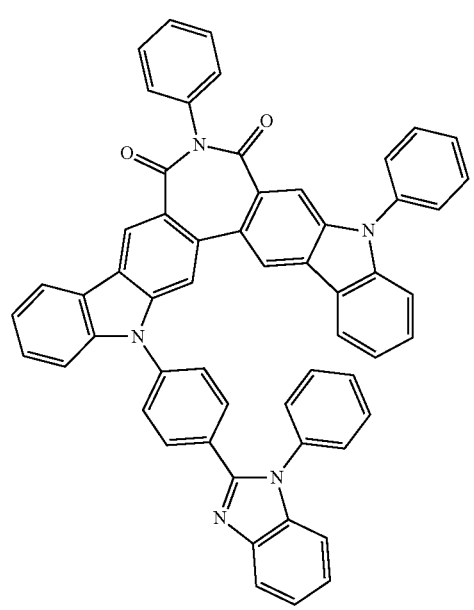
P75
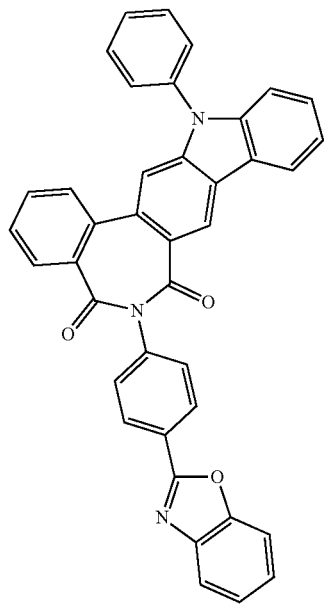
P76
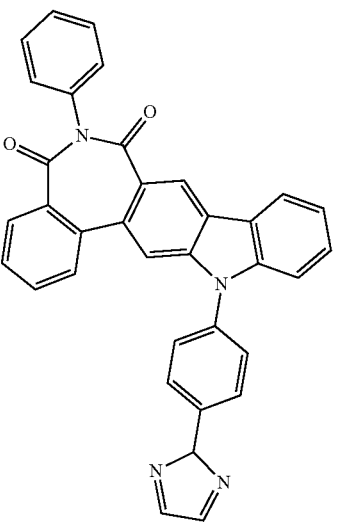

P77
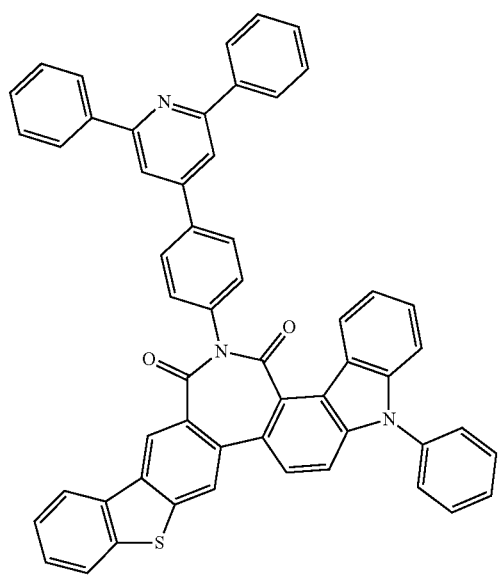
P78
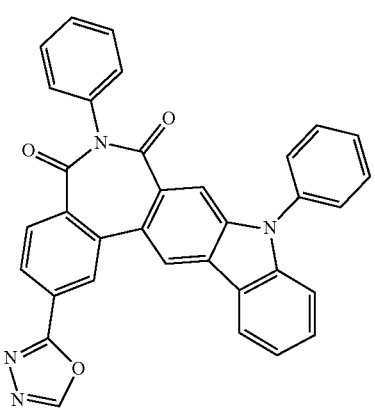
P79
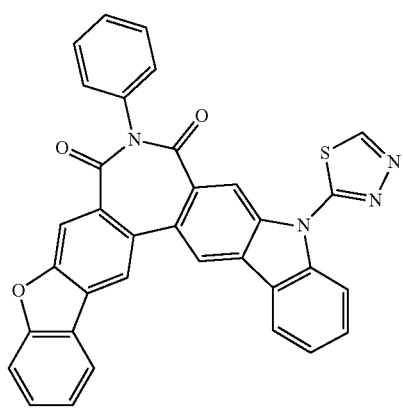
P80
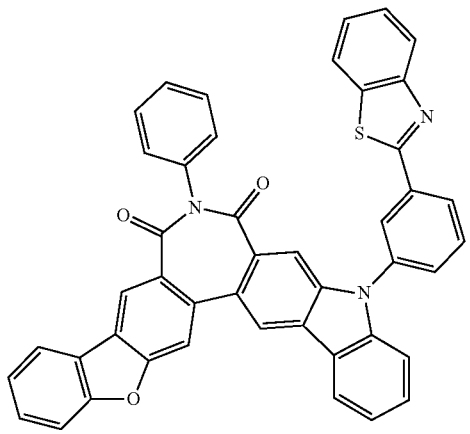
P81
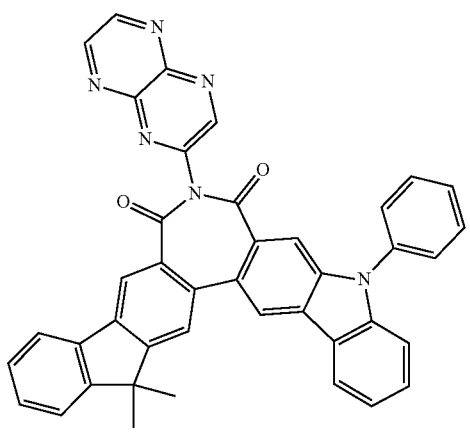
P82
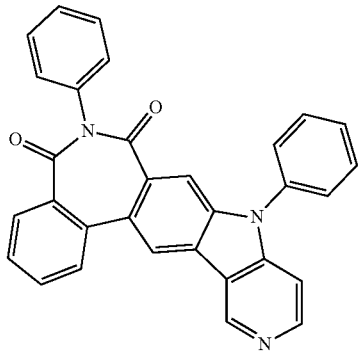
P83
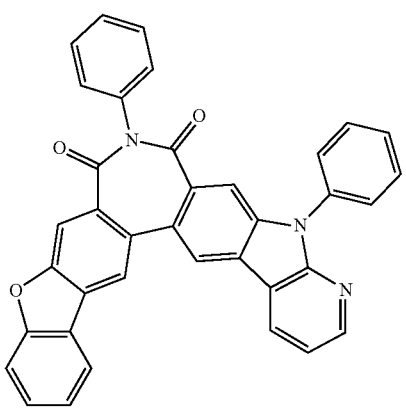

P84
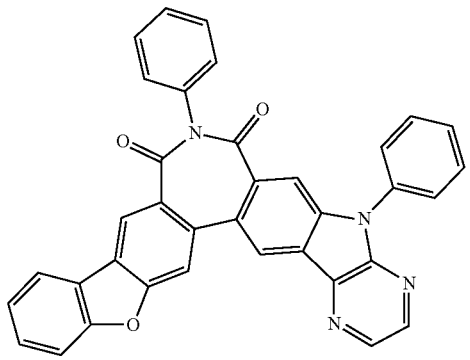
P85
P86
P87
P88
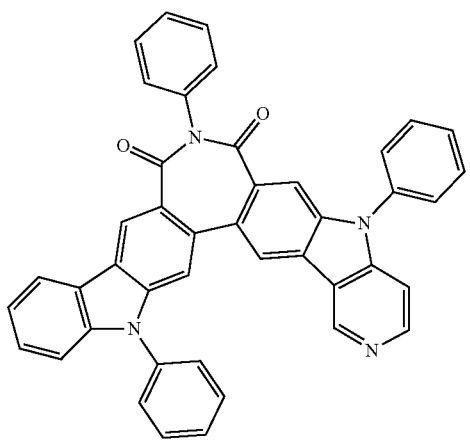
P89
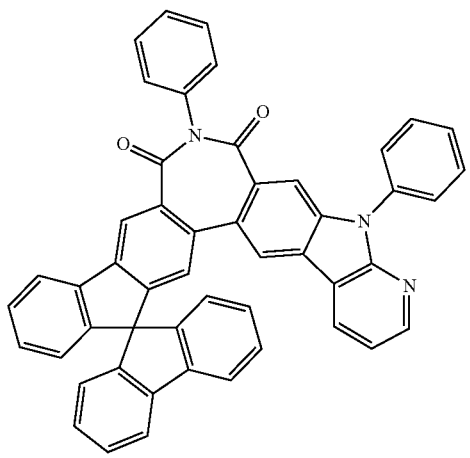
P90
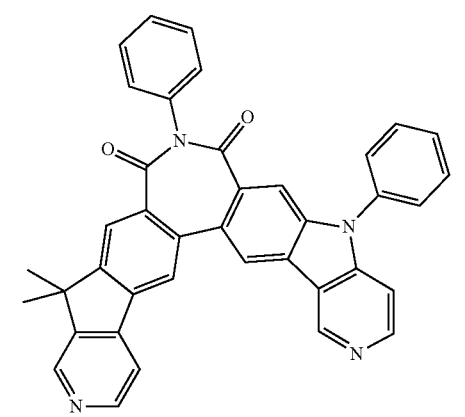

P91
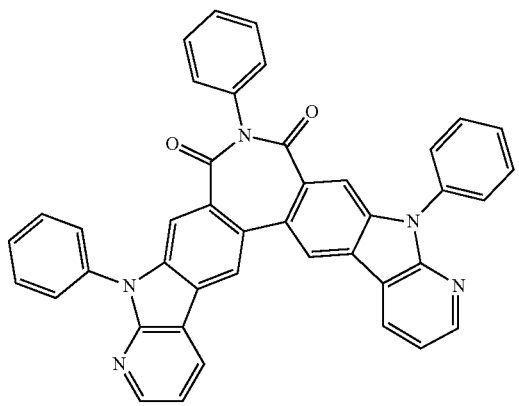
P92
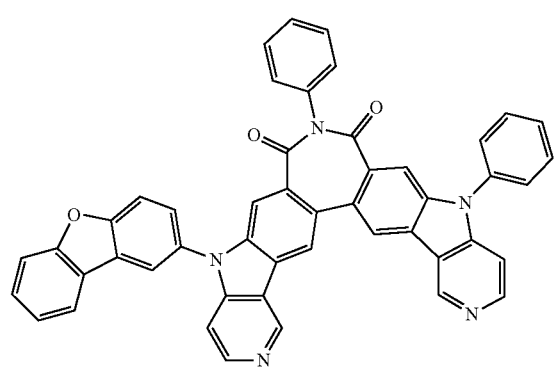
P93
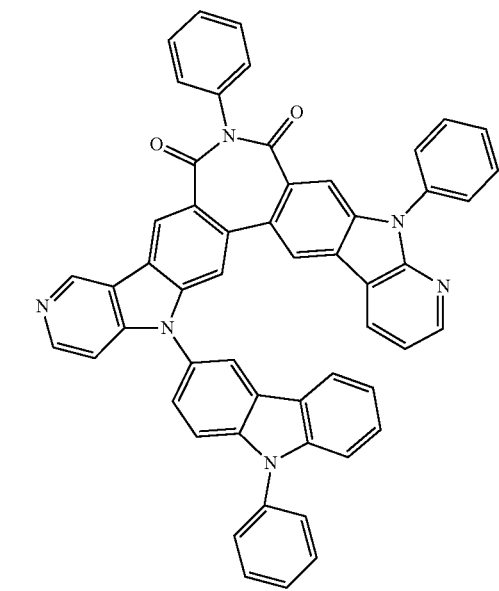
P94
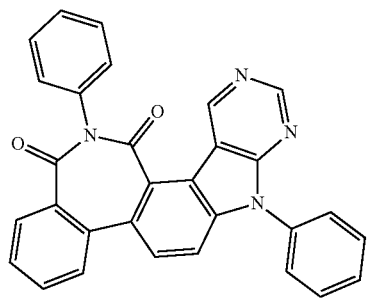
P95
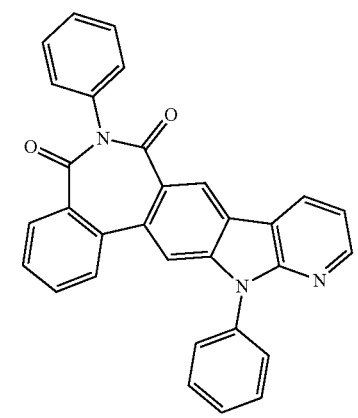
P96
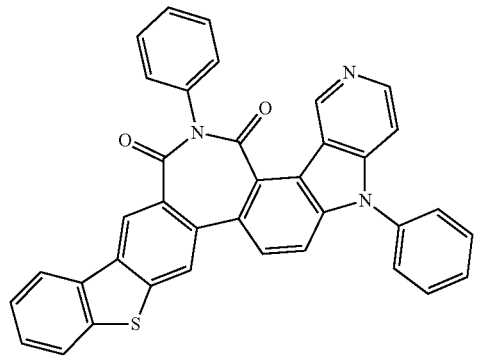
P97
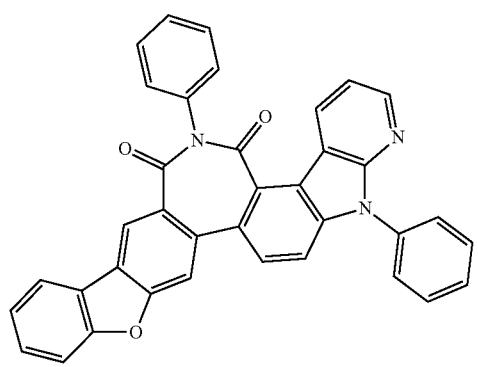

-continued
P98
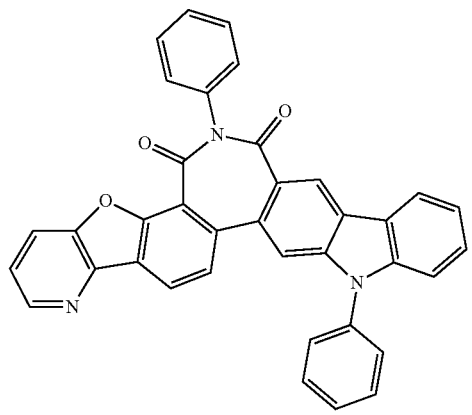
P99
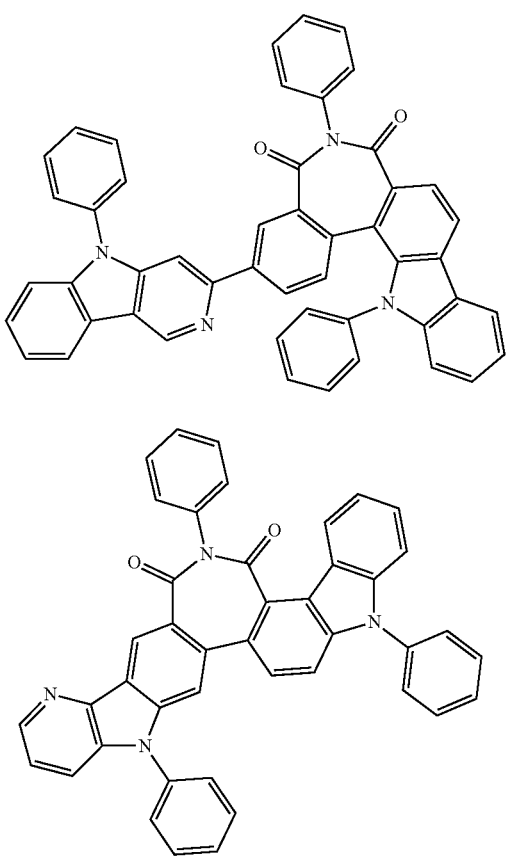
P100
P101
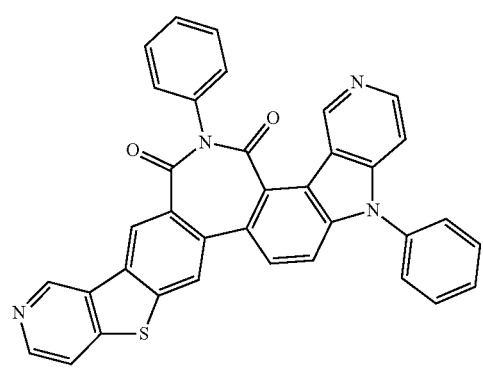
-continued
P102
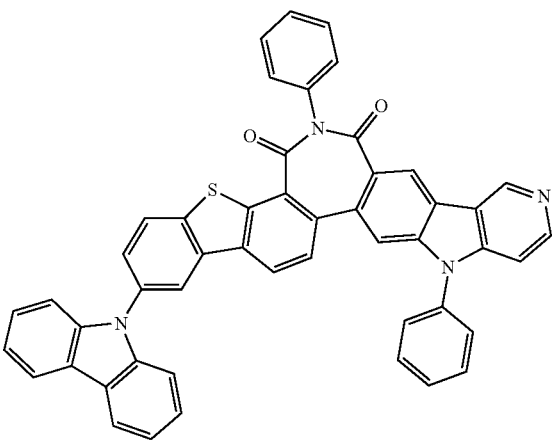
P103
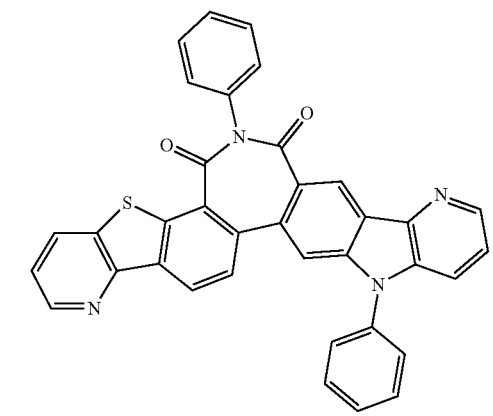
P104
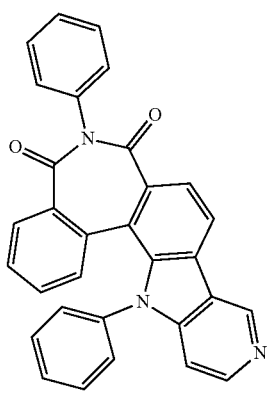

P105
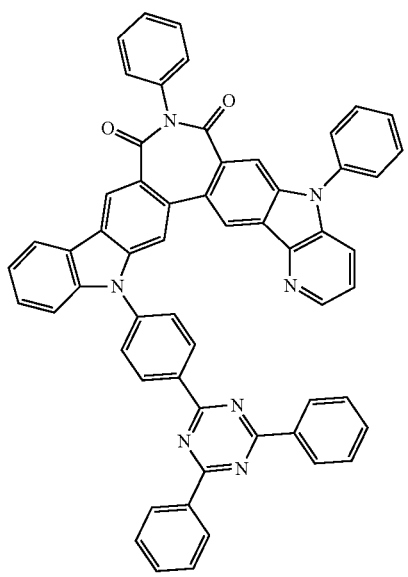
P106
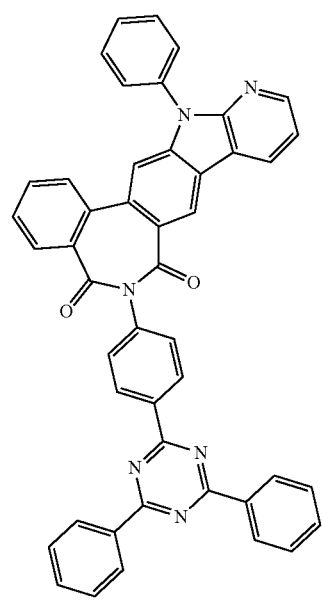
P107
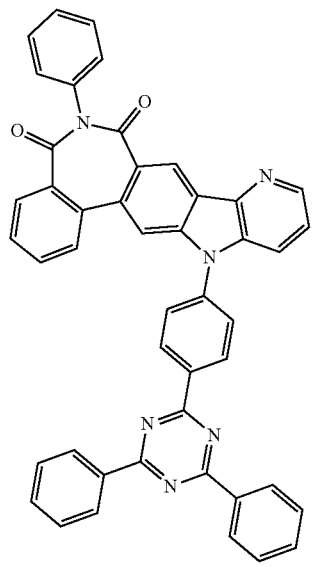
P108
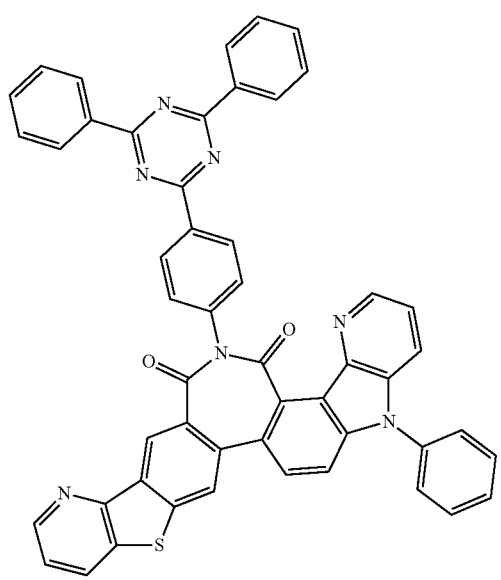
P109
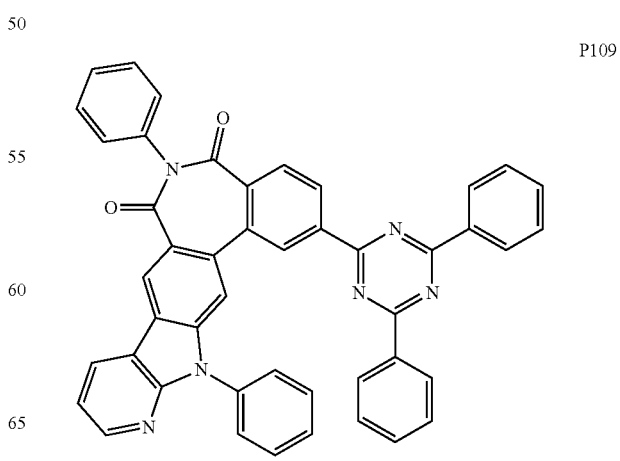

P110
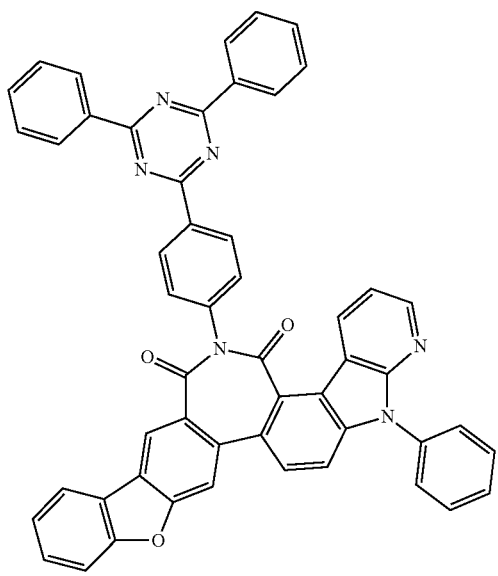
P111
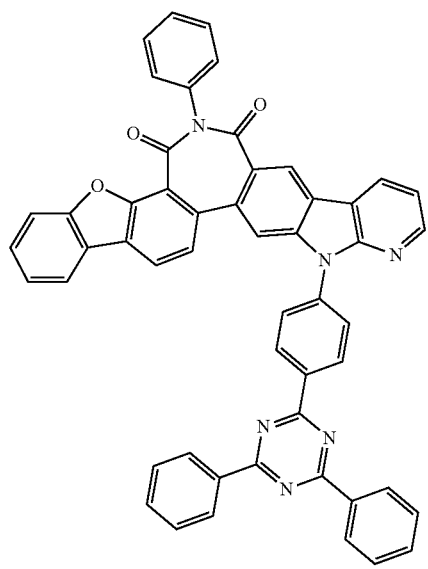
P112
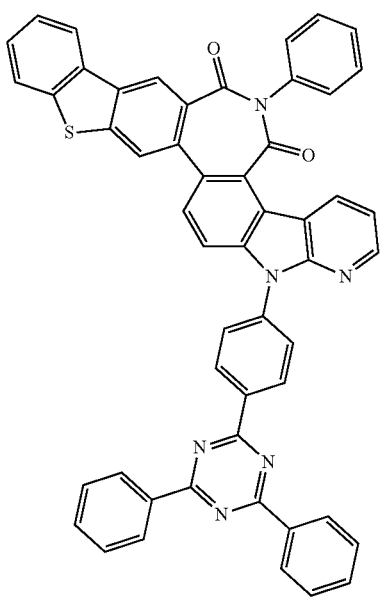
P113
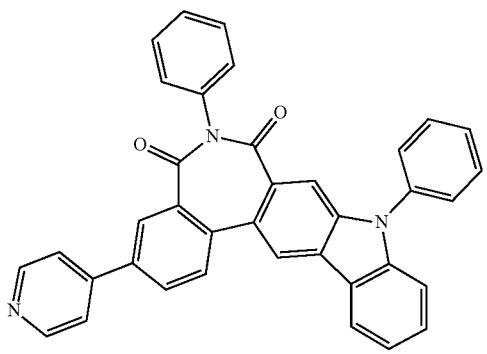
P114
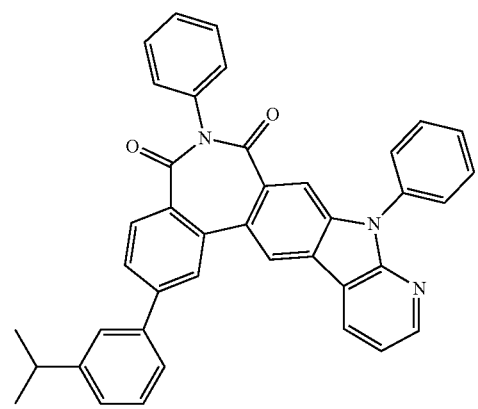

P115
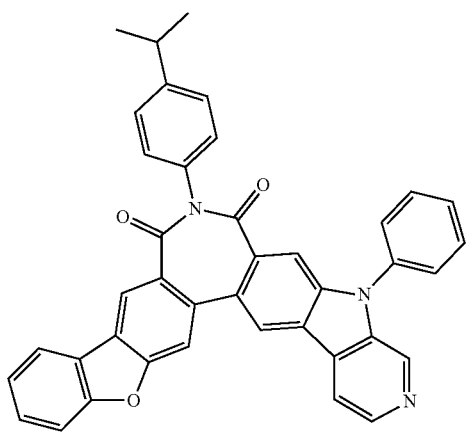
P116
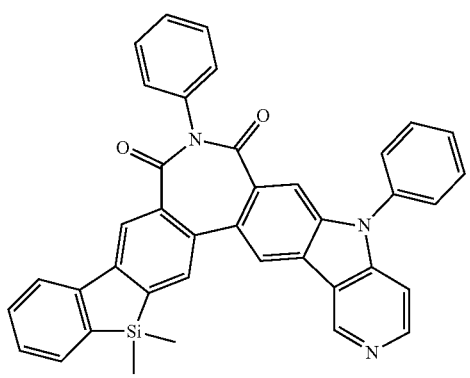
P117
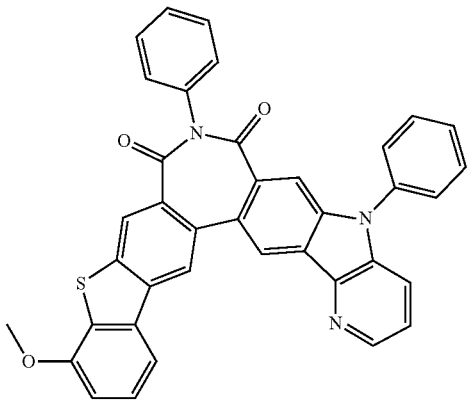
P118
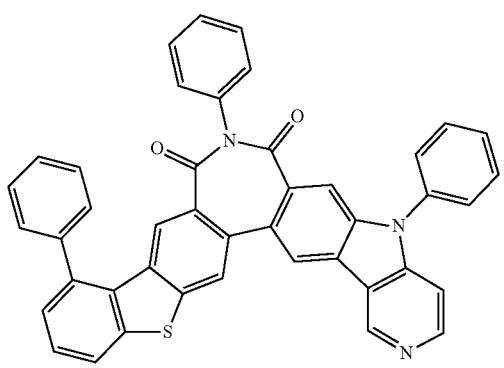
P119
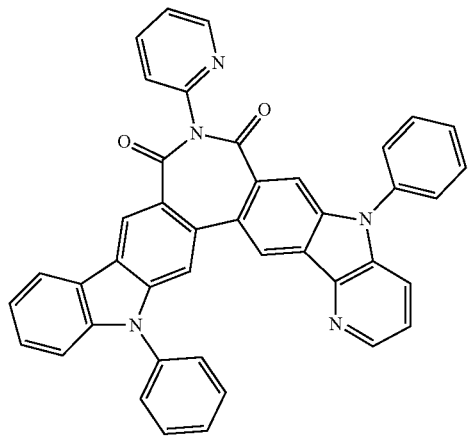
P120
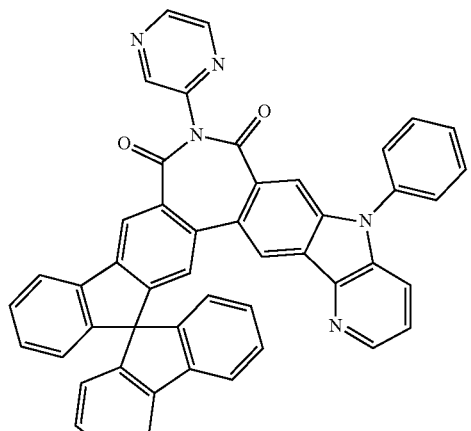
P121
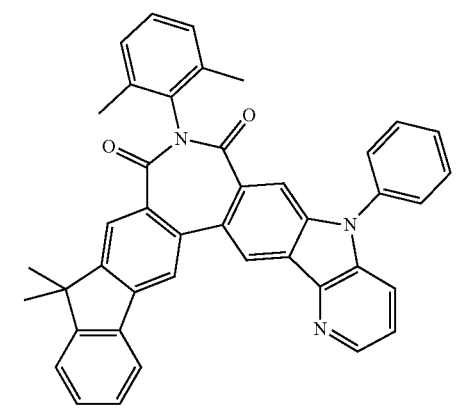

P122
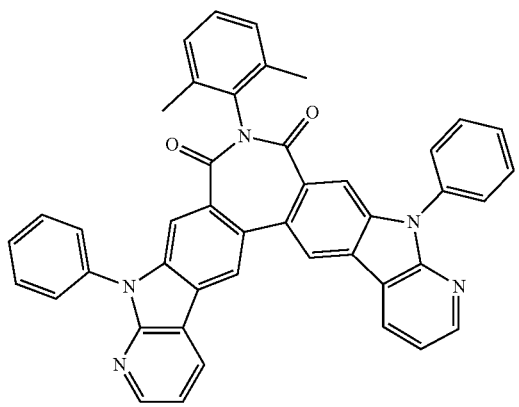
P123
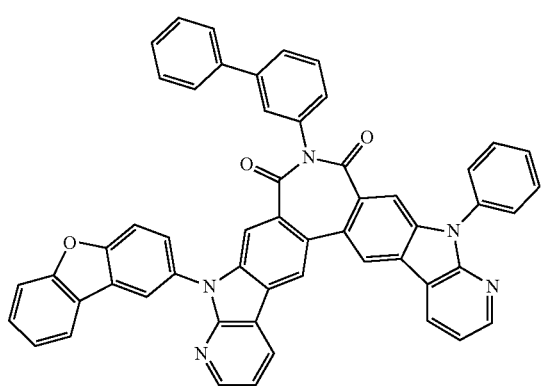
P124
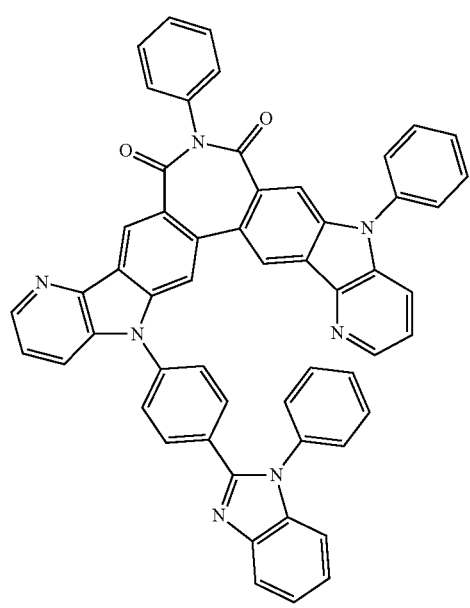
P125
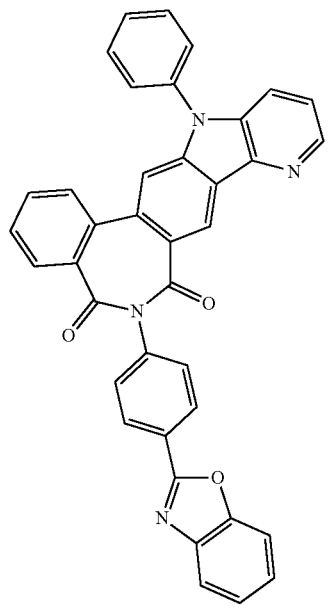
P126
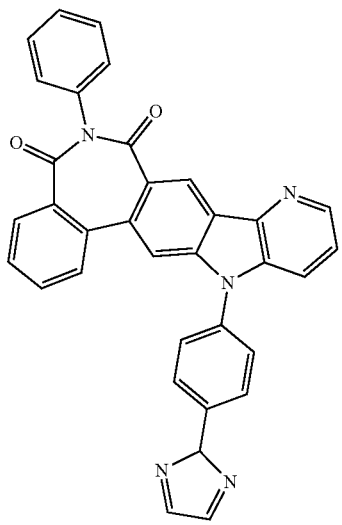

P127
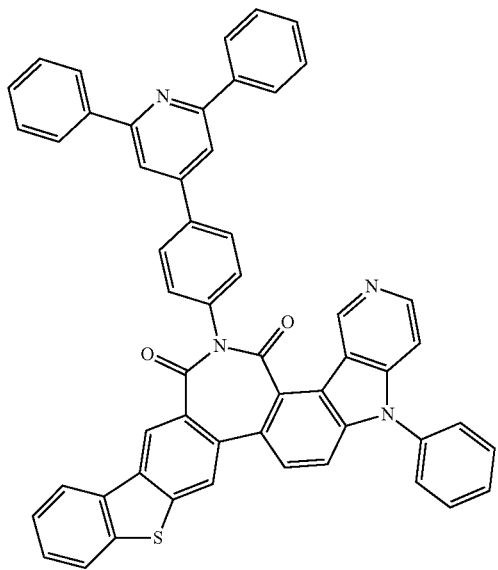
P128
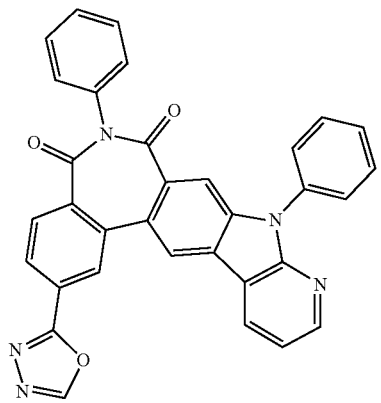
P129
P130
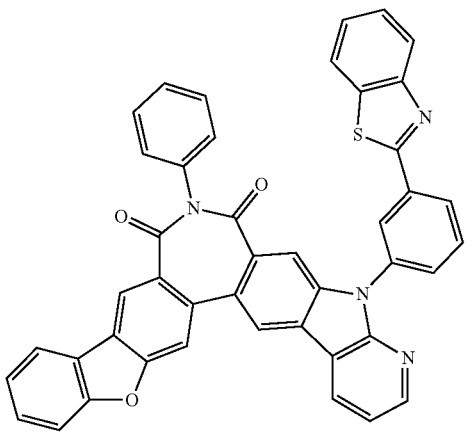
P131
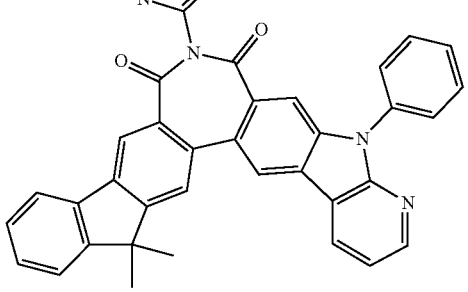
P132
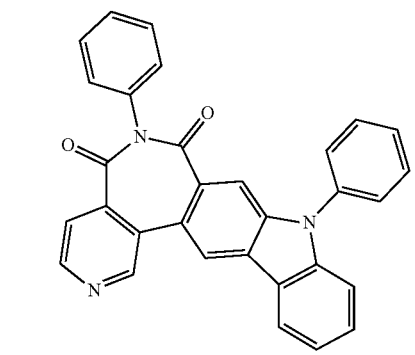
P133
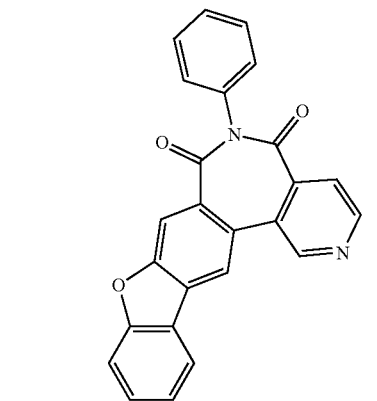

-continued
P134
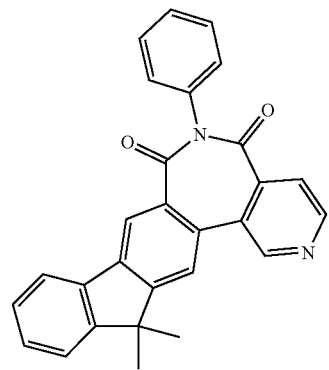
P135
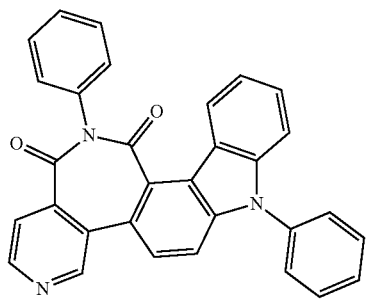
P136
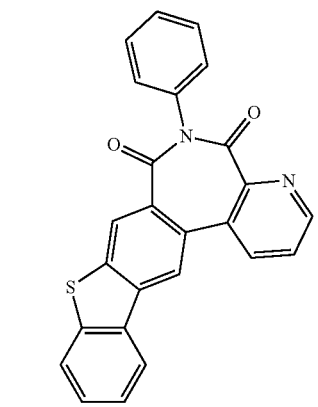
P137
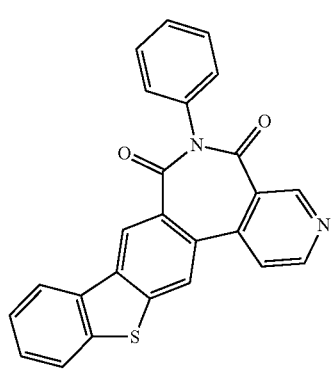
-continued
P138
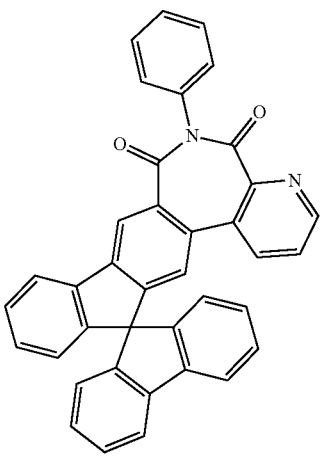
P139
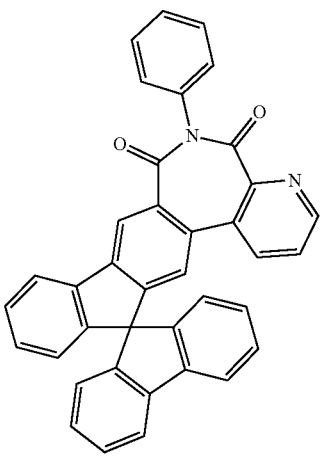
P140
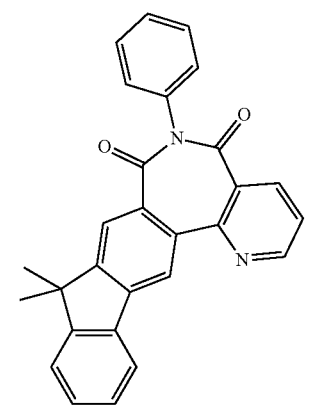

P141
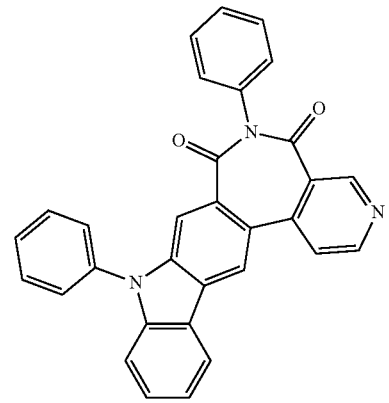
P142
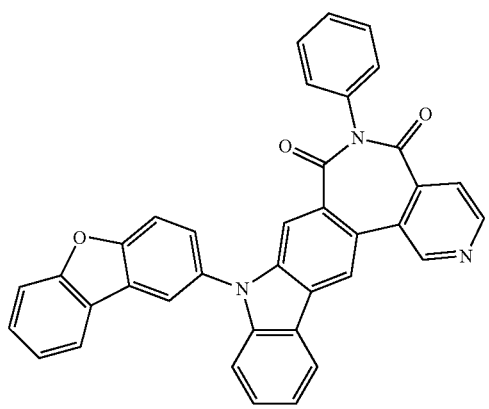
P143
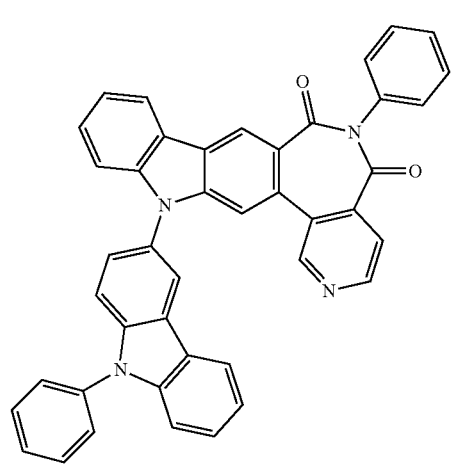
P144
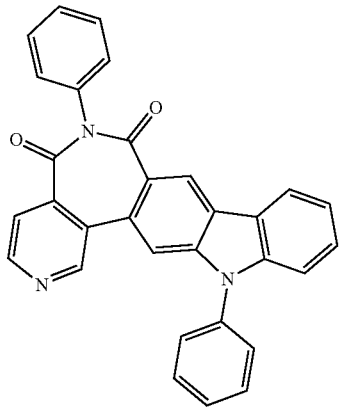
P145
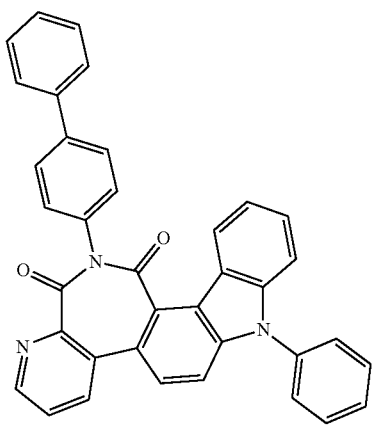
P146
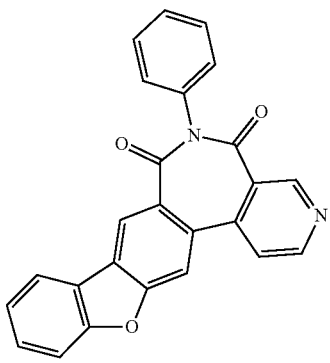
P147
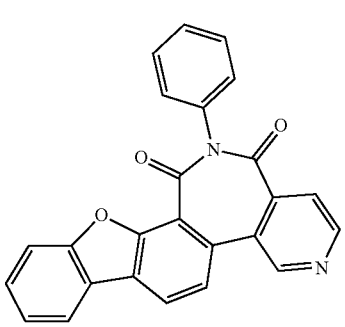

P148
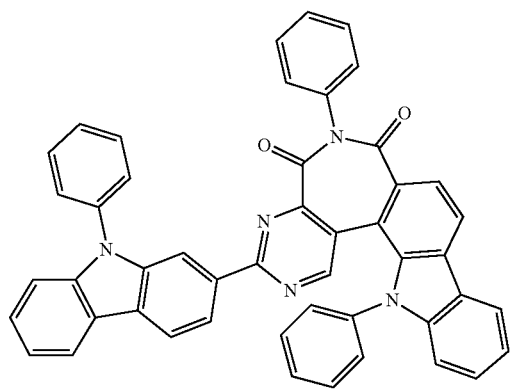
P149
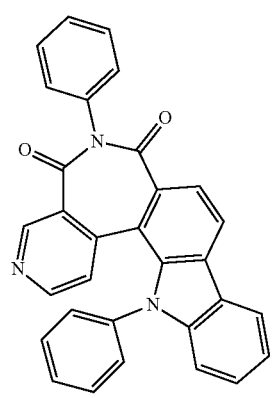
P150
P151
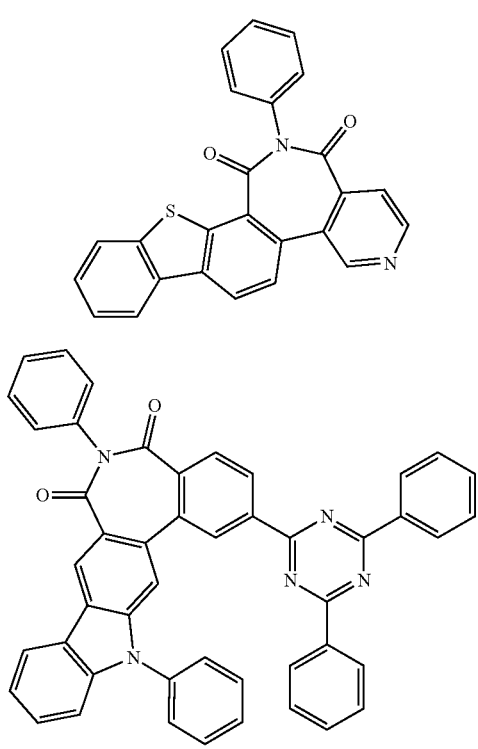
P152
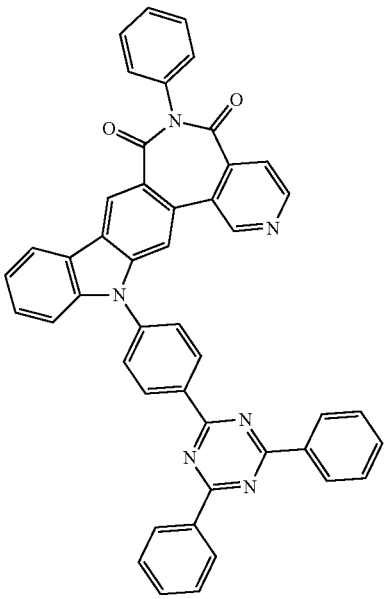
P153
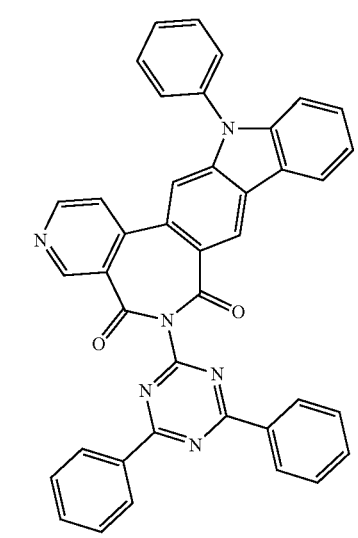

P154
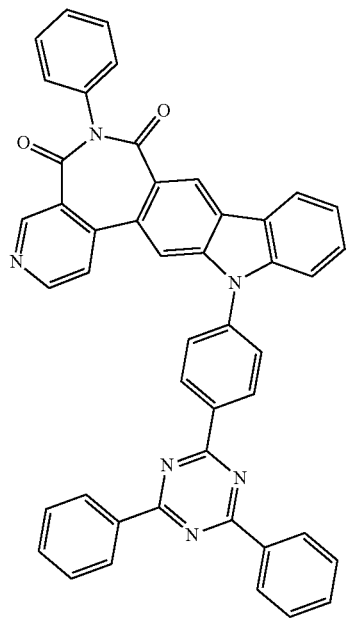
P155
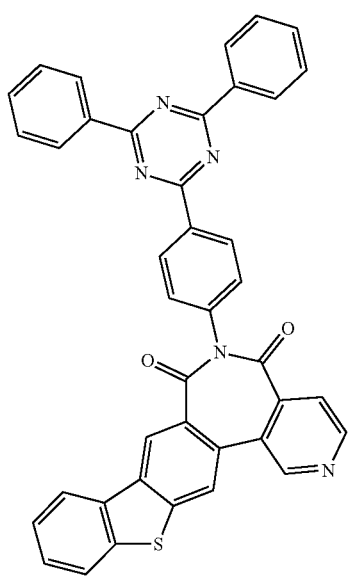
P156
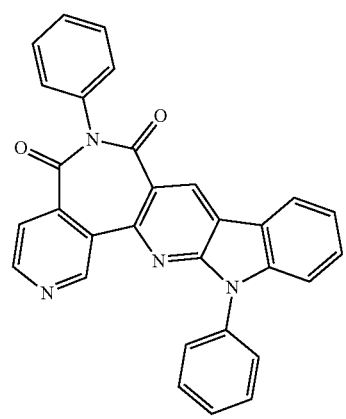
P157
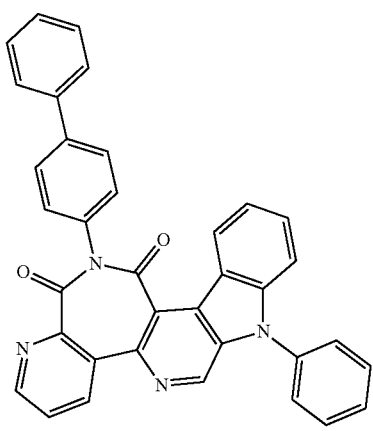
P158
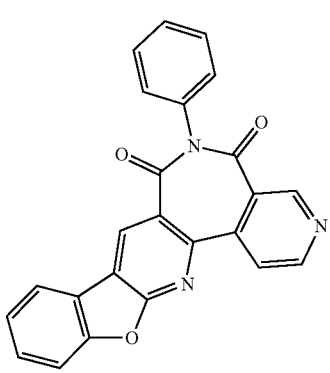
P159
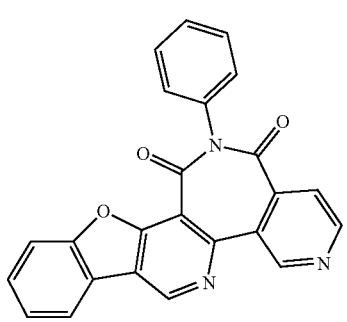
P160
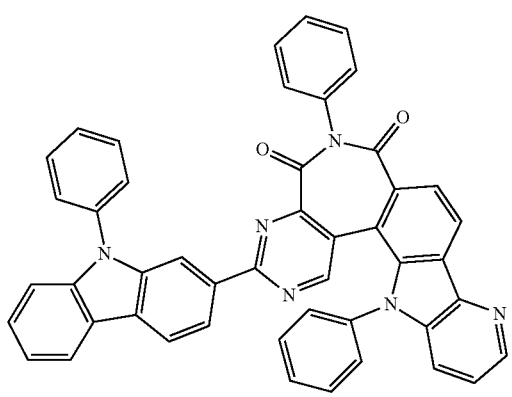

-continued
P161
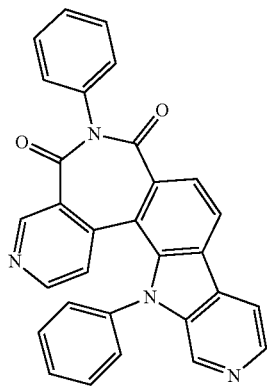
P162
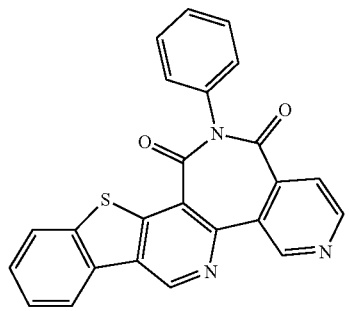
P163
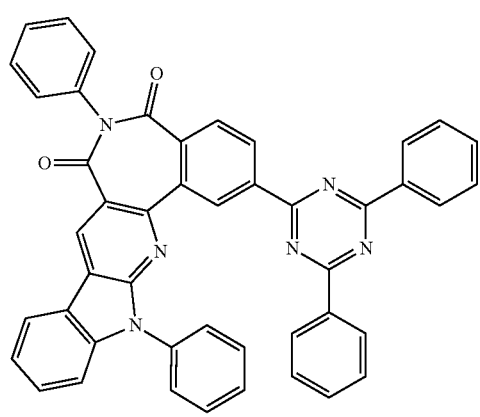
P164
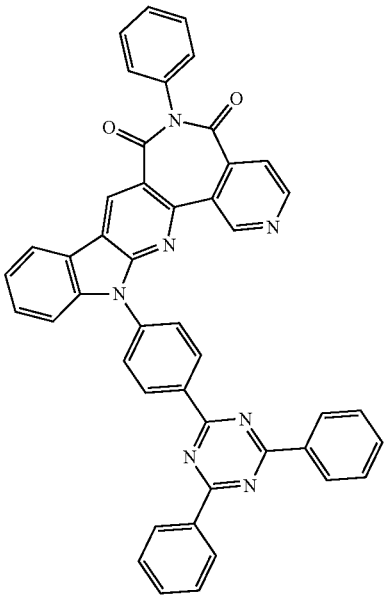
P165
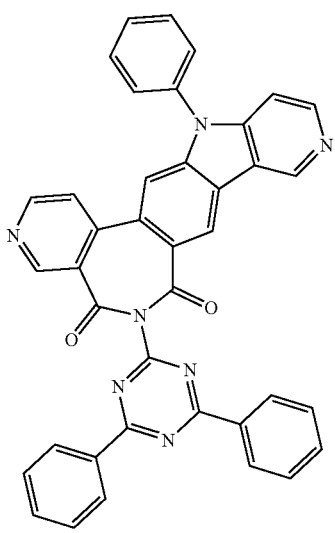

-continued
P166
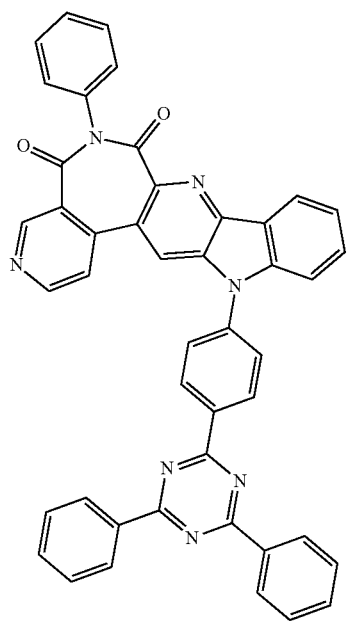
P167
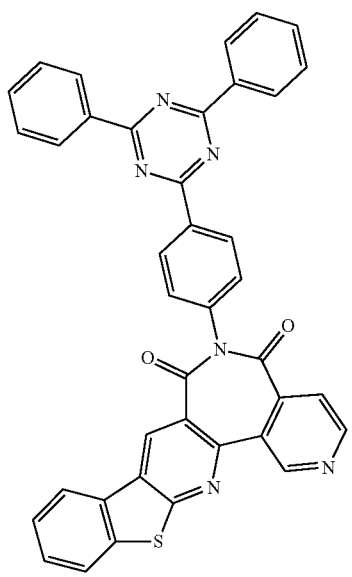
P168
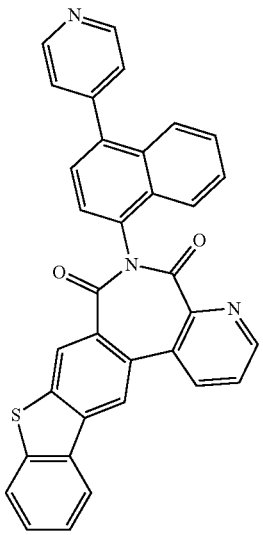
P169
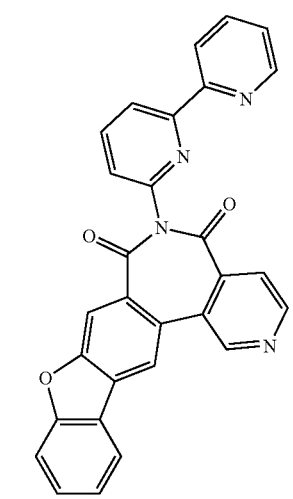
P170
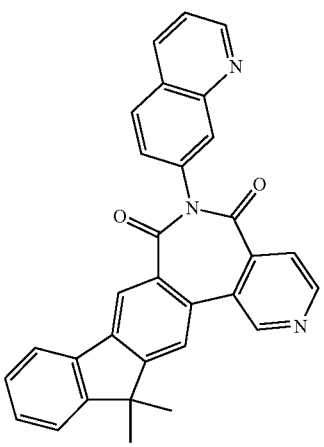

-continued
P171
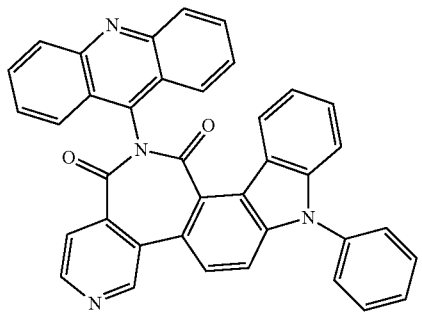
P172
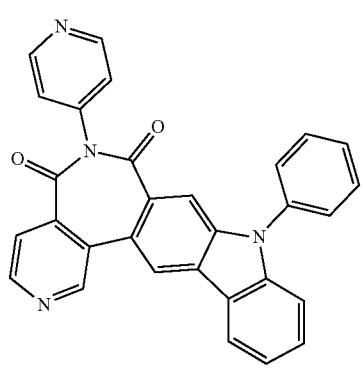
P173
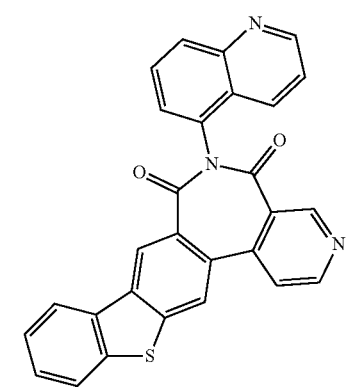
P174
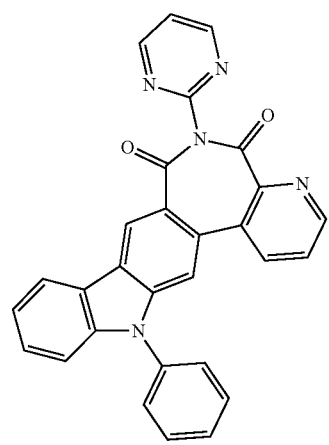
-continued
P175
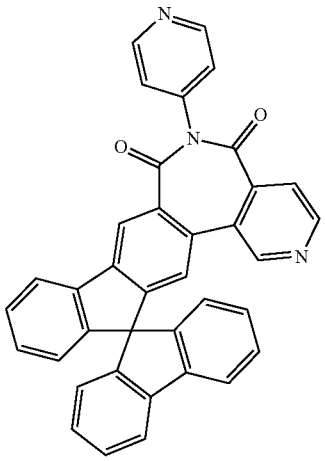
P176
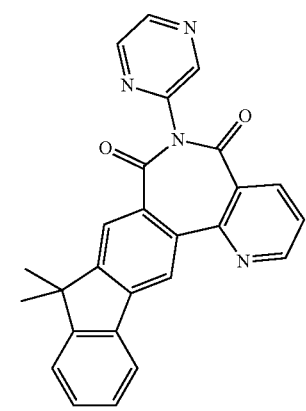
P177
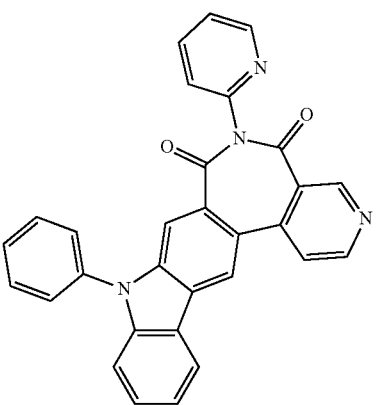

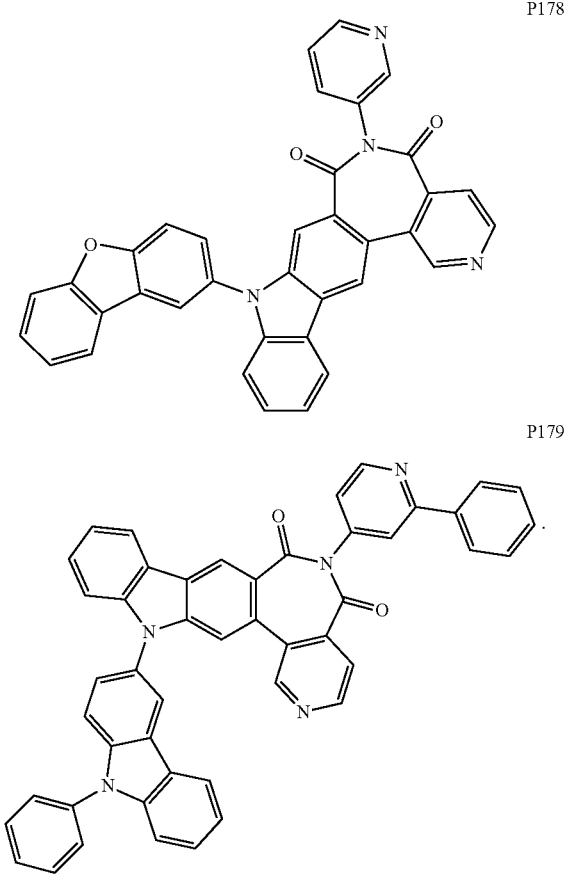

P178

P179

In an embodiment of the compound according to the present disclosure, the compound has a triple energy level ET greater than or equal to 2.6 eV.

In an embodiment of the compound according to the present disclosure, the compound has a glass transition temperature Tg greater than or equal to 120° C.

The compound according to the present disclosure can be used as a light-emitting host material, a hole transport material or a hole injection material.

The present disclosure further provides a display panel, including an organic light-emitting device. The organic light-emitting display device includes an anode, a cathode arranged oppositely to the anode, and a light-emitting layer disposed between the anode and the cathode. The light-emitting layer includes a host material and a guest material. The host material of the light-emitting layer is at least one of compounds according to the present disclosure.

In an embodiment of the display device according to the present disclosure, the organic light-emitting device further includes a hole transport layer, and a hole transport material of the hole transmission layer is at least one of compounds according to the present disclosure.

In an embodiment of the display device according to the present disclosure, the organic light-emitting device further comprises a hole injection layer, and a hole injection material of the hole injection layer is at least one of compounds according to the present disclosure.

In the display panel provided by the present disclosure, the anode of the organic light-emitting device can be made of metals, such as copper, gold, silver, iron, chromium, nickel, manganese, palladium, platinum, and alloys thereof; metal oxides, such as indium oxide, zinc oxide, indium tin oxide (ITO), indium zinc oxide (IZO), and the like; conductive polymers, such as polyaniline, polypyrrole, poly(3-methylthiophene) and the like; other anode materials known in the art that are conductive to injecting holes; or combinations thereof.

In the display panel provided by the present disclosure, the cathode of the organic light-emitting device can be made of metals, such as aluminum, magnesium, silver, indium, tin, titanium, etc., or alloys thereof; multiple-layered metal materials, such as LiF/Al, LiO$_2$/Al, BaF$_2$/Al, and the like; other suitable materials for the cathode which is conductive to injecting holes; or combinations thereof.

In the present disclosure, the organic light-emitting device is manufactured by following steps: forming an anode on a transparent or opaque smooth substrate; forming an organic layer on the anode; and forming a cathode on the organic layer. The organic layer can be formed by a known method such as vapor deposition, sputtering, spin coating, dipping, ion plating, and the like. The organic layer at least includes a hole transport layer and a light-emitting layer. The hole transport layer includes one or more compounds according to the present disclosure. The organic layer may further includes an electron blocking layer made of one or more compounds according to the present disclosure.

In another aspect of the present disclosure, the synthesis of Compound P1, Compound P10, Compound P25, Compound P28, Compound P32 and Compound P133 are described as examples.

Example 1

Synthesis of Compound P1, with the following synthesis scheme:

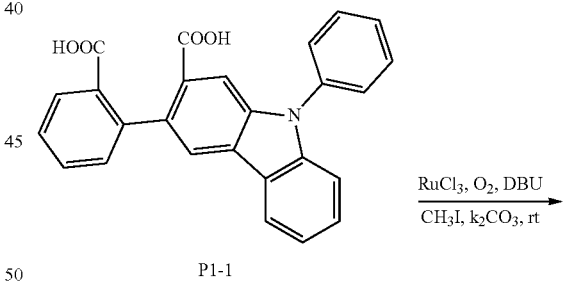

P1-1

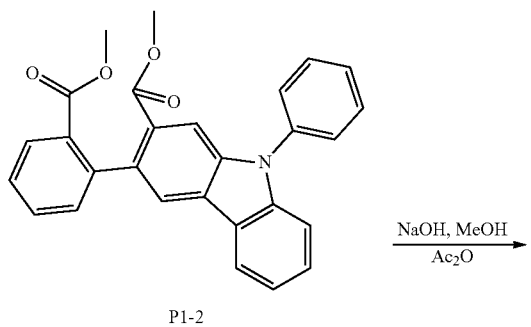

P1-2

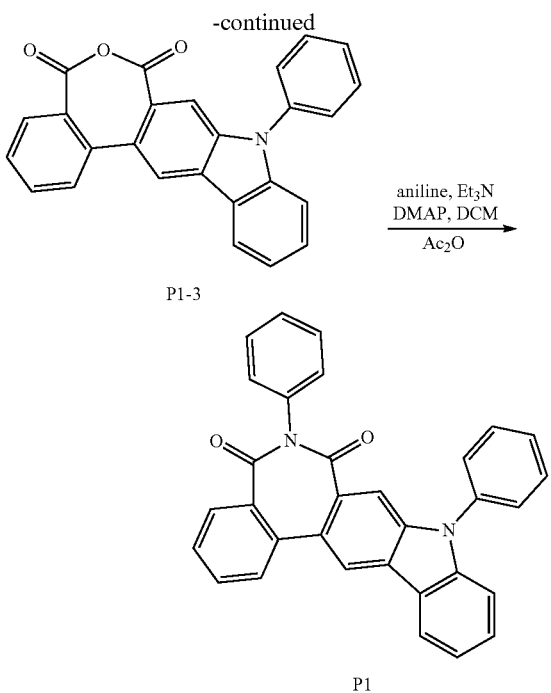

P1-3

P1

The synthesis includes the following steps:

(1) Compound P1-1 (10.0 mmol), RuCl$_3$ (1.0 mmol), 1,8-diazabicycloundec-7-ene (DBU, 10.0 mmol) were dissolved in DME (25 mL), and reacted at 110° C. for 30 h in an oxygen environment. After cooling to room temperature, iodomethane (50.0 mmol) and K$_2$CO$_3$ (50.0 mmol) were added and stirred for reaction for 6 h at room temperature. After the reaction was finished, the mixture was extracted with ethyl acetate, then washed with 50 mL of water three times, and dried over anhydrous magnesium sulfate. After filtration and evaporation, the organic phase was evaporated by rotary evaporation to remove solvent. The crude product was purified with silica gel column chromatography using an eluent of ethyl acetate/petroleum ether (1:5, volume ratio), to obtain a solid product P1-2.

The product P1-2 was analyzed with matrix-assisted laser desorption ionization time-of-flight mass spectrometry (MALDI-TOF MS (m/z): C$_{28}$H$_{21}$NO$_4$, calculated 435.2, measured 435.1.

(2) The intermediate P1-2 (3.0 mmol) was dissolved in a solution (160 mL) of methylhydrofuran/methanol (THF/CH$_3$OH)=3:1, NaOH (5.0 mmol) was added, and under a nitrogen atmosphere, the mixture was refluxed to react for 6 h. Then the reaction solution was cooled to room temperature, the solvent was removed by distillation under reduced pressure, the remaining solid was dissolved in 150 mL of water, and then added to HCl solution (6M, 18 mL) to be acidified, and then filtered to obtain a white solid. After vacuum drying, the solid was dissolved in 15 mL of acetic anhydride and refluxed for 6 h and then cooled to room temperature, and the solvent was removed by distillation under reduced pressure to obtain an intermediate P1-3.

The product P1-3 was analyzed with matrix-assisted laser desorption ionization time-of-flight mass spectrometry (MALDI-TOF MS (m/z): C$_{26}$H$_{15}$NO$_3$, calculated 389.1, measured 389.3.

(3) The intermediate P1-3 (2.0 mmol), aniline (2.4 mmol), 4-dimethylaminopyridine (DMAP, 0.04 mmol) and Et$_3$N (6.0 mmol) were added to dry dichloromethane (DCM, 20 mL), and the mixture reacted under nitrogen atmosphere at room temperature for 12 h. Then HCl solution (2 mmol/L) was added, and then the mixed solution was extracted with DCM, and washed with water, dried over anhydrous sodium sulfate. After filtration and evaporation, 20 mL of acetic anhydride was added and the mixture was refluxed under stirring for 6 h. After cooling to room temperature, the solvent was removed by distillation under reduced pressure, and the crude product was purified by silica gel column chromatography to obtain Compound P1.

The product P1 was analyzed with matrix-assisted laser desorption ionization time-of-flight mass spectrometry (MALDI-TOF MS (m/z): C$_{32}$H$_{20}$N$_2$O$_2$, calculated 464.2, measured 464.0.

Elemental analysis: theoretical: C, 82.74; H, 4.34; N, 6.03; measured C, 82.75; H, 4.34; N, 6.02.

Example 2

Synthesis of Compound P10, with the following synthesis scheme:

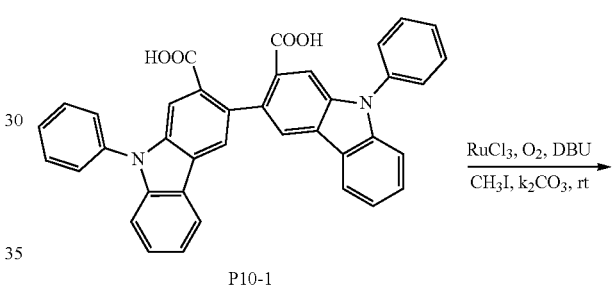

P10-1

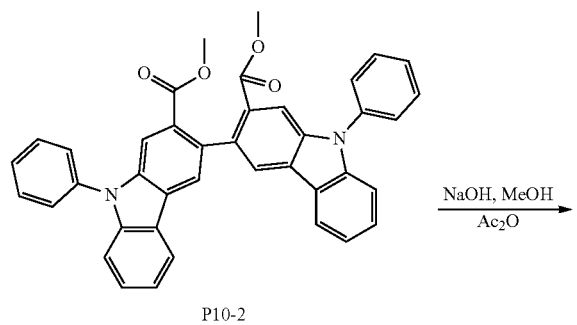

P10-2

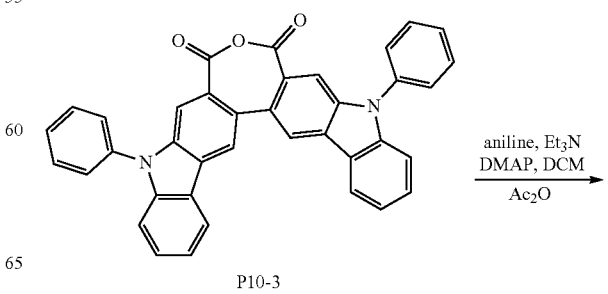

P10-3

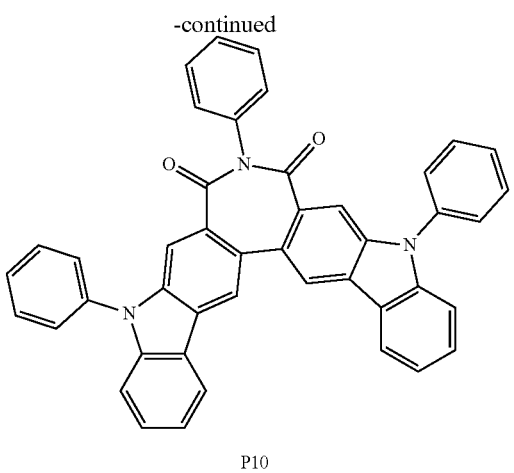

P10

The synthesis includes the following steps:

(1) Compound P10-1 (10.0 mmol), RuCl$_3$ (1.0 mmol), DBU (10.0 mmol) were dissolved in DME (25 mL), and reacted at 110° C. for 30 h in an oxygen environment. After cooling to room temperature, iodomethane (50.0 mmol) and K$_2$CO$_3$ (50.0 mmol) were added and stirred for 6 h at room temperature. After the reaction was finished, the mixture was extracted with ethyl acetate, then washed with 50 mL of water three times, and dried over anhydrous magnesium sulfate. After filtration and evaporation, the organic phase was evaporated by rotary evaporation to remove solvent. The crude product was purified with silica gel column chromatography using an eluent of ethyl acetate/petroleum ether (1:5, volume ratio), to obtain a solid product P10-2.

The target product P10-2 was analyzed with matrix-assisted laser desorption ionization time-of-flight mass spectrometry (MALDI-TOF MS (m/z): C$_{40}$H$_{28}$N$_2$O$_4$, calculated 600.2, measured 600.1.

(2) The intermediate P10-2 (3.0 mmol) was dissolved in a solution (160 mL) of THF/CH$_3$OH (=3:1), NaOH (5.0 mmol) was added, and under a nitrogen atmosphere, the mixture was refluxed to react for 6 h. Then the reaction solution was cooled to room temperature, the solvent was removed by distillation under reduced pressure, the remaining solid was dissolved in 150 mL of water, and then added to HCl solution (6M, 18 mL) to be acidified, and then filtered to obtain a white solid. After vacuum drying, the solid was dissolved in 15 mL of acetic anhydride, refluxed for 6 h, and then cooled to room temperature, and the solvent was removed by distillation under reduced pressure to obtain an intermediate P10-3.

The product P10-3 was analyzed with matrix-assisted laser desorption ionization time-of-flight mass spectrometry (MALDI-TOF MS (m/z): C$_{38}$H$_{22}$N$_2$O$_3$, calculated 554.2, measured 554.3.

(3) The intermediate P10-3 (2.0 mmol), aniline (2.4 mmol), DMAP (0.04 mmol) and Et$_3$N (6.0 mmol) were added to dry DCM (20 mL), and the mixture reacted under nitrogen atmosphere at room temperature for 12 h. Then HCl solution (2 mmol/L) was added, and then the mixed solution was extracted with DCM, washed with water, and dried over anhydrous sodium sulfate. After filtration and evaporation, 20 mL of acetic anhydride was added and the mixture was refluxed under stirring for 6 h. After cooling to room temperature, the solvent was removed by distillation under reduced pressure, and the crude product was purified by silica gel column chromatography to obtain Compound P10.

The product P10 was analyzed with matrix-assisted laser desorption ionization time-of-flight mass spectrometry (MALDI-TOF MS (m/z): C$_{44}$H$_{27}$N$_3$O$_2$, calculated 629.2, measured 629.0.

Elemental analysis: theoretical: C, 83.92; H, 4.32; N, 6.67; measured C, 83.92; H, 4.34; N, 6.66.

Example 3

Synthesis of Compound P25, with the following synthesis scheme:

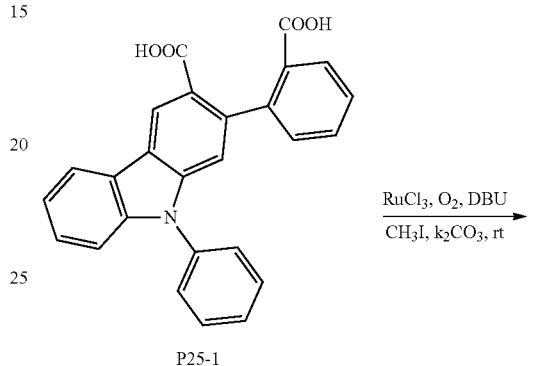

P25-1

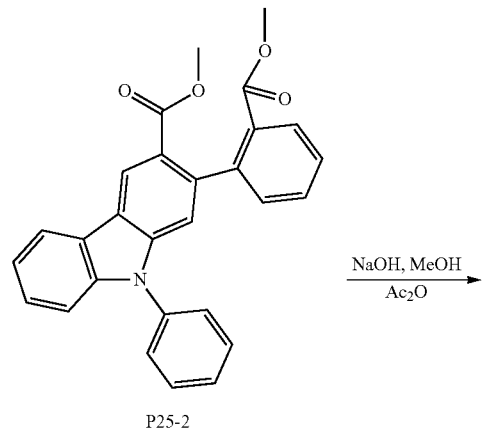

P25-2

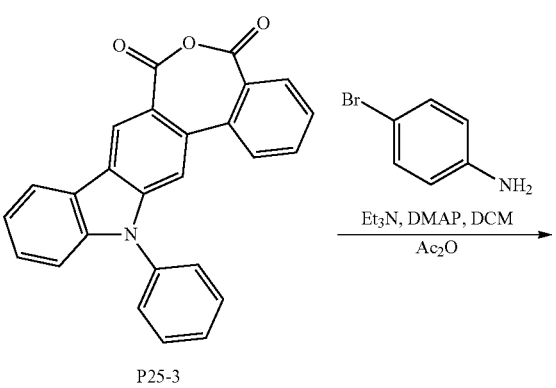

P25-3

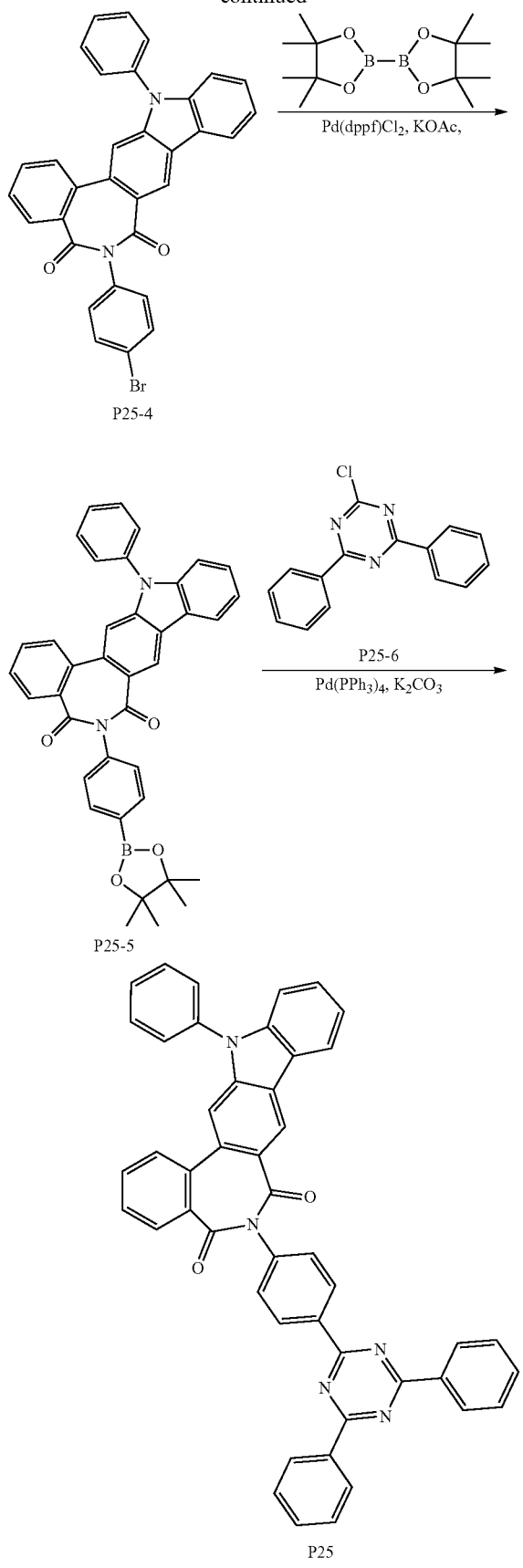

The synthesis includes the following steps:

(1) Compound P25-1 (10.0 mmol), RuCl$_3$ (1.0 mmol), and DBU (10.0 mmol) were dissolved in DME (25 mL), and reacted at 110° C. for 30 h in an oxygen environment. After cooling to room temperature, iodomethane (50.0 mmol) and K$_2$CO$_3$ (50.0 mmol) were added and stirred for reaction for 6 h at room temperature. After the reaction was finished, the mixture was extracted with ethyl acetate, then washed with 50 mL of water three times, and dried over anhydrous magnesium sulfate. After filtration and evaporation, the organic phase was evaporated by rotary evaporation to remove solvent. The crude product was purified with silica gel column chromatography using an eluent of ethyl acetate/petroleum ether (1:5, volume ratio), to obtain a solid product P25-2.

The product P25-2 was analyzed with matrix-assisted laser desorption ionization time-of-flight mass spectrometry (MALDI-TOF MS (m/z): C$_{28}$H$_{21}$NO$_4$, calculated 435.2, measured 435.1.

(2) The intermediate P25-2 (3.0 mmol) was dissolved in a solution (160 mL) of THF/CH$_3$OH (=3:1), NaOH (5.0 mmol) was added, and under a nitrogen atmosphere, the mixture was refluxed to react for 6 h. Then the reaction solution was cooled to room temperature, the solvent was removed by distillation under reduced pressure, the remaining solid was dissolved in 150 mL of water, and then added to HCl solution (6M, 18 mL) to be acidified, and then filtered to obtain a white solid. After vacuum drying, the solid was dissolved in 15 mL of acetic anhydride and refluxed for 6 h and then cooled to room temperature, and the solvent was removed by distillation under reduced pressure to obtain an intermediate P25-3.

The product P25-3 was analyzed with matrix-assisted laser desorption ionization time-of-flight mass spectrometry (MALDI-TOF MS (m/z): C26H$_{15}$NO$_3$, calculated 389.1, measured 389.3.

(3) The intermediate P25-3 (2.0 mmol), 4-bromoaniline (2.4 mmol), DMAP (0.04 mmol) and Et$_3$N (6.0 mmol) were added to dry DCM (20 mL), and the mixture reacted under nitrogen atmosphere at room temperature for 12 h. Then HCl solution (2 mmol/L) was added, and then the mixed solution was extracted with DCM, washed with water, and dried over anhydrous sodium sulfate. After filtration and evaporation, 20 mL of acetic anhydride was added and the mixture was refluxed under stirring for 6 h. After cooling to room temperature, the solvent was removed by distillation under reduced pressure, and the crude product was purified by silica gel column chromatography to obtain Compound P25-4.

The product P25-4 was analyzed with matrix-assisted laser desorption ionization time-of-flight mass spectrometry (MALDI-TOF MS (m/z): C$_{32}$H$_{19}$BrN$_2$O$_2$, calculated 542.1, measured 542.0.

(4) The intermediate product P25-4 (1.5 mmol) and potassium acetate (4.0 mmol) were mixed with dry 1,4-dioxane (20 mL), Pd(dppf)Cl$_2$ (0.1 mmol) and bis(pinacolato)diboron (5.0 mmol) and stirred for 48 h at 90° C. under a nitrogen atmosphere. The obtained intermediate was cooled to room temperature and added to water, and then filtered through a pad of diatomite. The filtrate was extracted with dichloromethane, then washed with water, and dried over anhydrous magnesium sulfate. After filtration and evaporation, the crude product was purified with silica gel column chromatography to obtain the intermediate product P25-5.

The product P25-5 was analyzed with matrix-assisted laser desorption ionization time-of-flight mass spectrometry (MALDI-TOF MS (m/z): $C_{38}H_{31}BN_2O_4$, calculated 590.2, measured 590.0.

(5) P25-5 (2.0 mmol), P25-6 (2.0 mmol) and $Pd(PPh_3)_4$ (0.2 mmol) were added to a mixture of toluene (30 mL)/ ethanol (20 mL), potassium carbonate (24 mmol) and water (20 mL), and refluxed for reaction for 12 h under a nitrogen atmosphere. The obtained mixture was cooled to room temperature, added to water, and then filtered through a pad of diatomite, and the filtrate was extracted with dichloromethane, then washed with water, and dried over anhydrous magnesium sulfate. After filtration and evaporation, the crude product was purified with silica gel column chromatography to obtain the final product P25.

The product P25 was analyzed with matrix-assisted laser desorption ionization time-of-flight mass spectrometry (MALDI-TOF MS (m/z): $C_{47}H_{29}N_5O_2$, calculated 695.2, measured 695.0.

Elemental analysis: theoretical: C, 81.13; H, 4.20; N, 10.07; measured C, 81.13; H, 4.21; N, 10.06.

Example 4

Synthesis of Compound P28, with the following synthesis scheme:

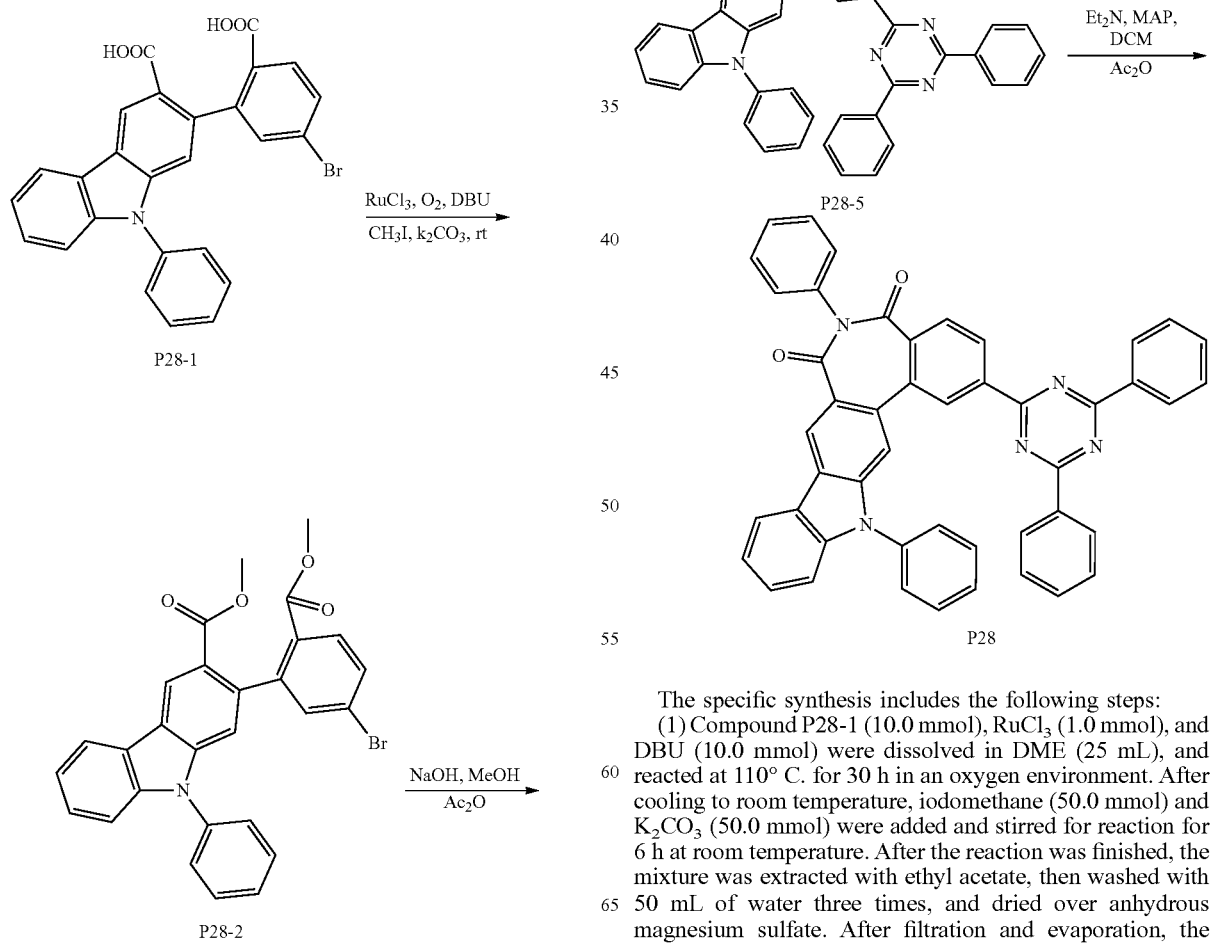

The specific synthesis includes the following steps:
(1) Compound P28-1 (10.0 mmol), $RuCl_3$ (1.0 mmol), and DBU (10.0 mmol) were dissolved in DME (25 mL), and reacted at 110° C. for 30 h in an oxygen environment. After cooling to room temperature, iodomethane (50.0 mmol) and $K_2CO_3$ (50.0 mmol) were added and stirred for reaction for 6 h at room temperature. After the reaction was finished, the mixture was extracted with ethyl acetate, then washed with 50 mL of water three times, and dried over anhydrous magnesium sulfate. After filtration and evaporation, the organic phase was evaporated by rotary evaporation to remove solvent. The crude product was purified with silica gel column chromatography using an eluent of ethyl acetate/petroleum ether (1:5, volume ratio), to obtain a solid product P28-2.

The product P28-2 was analyzed with matrix-assisted laser desorption ionization time-of-flight mass spectrometry (MALDI-TOF MS (m/z): $C_{28}H_{20}BrNO_4$, calculated 513.1, measured 513.2.

(2) The intermediate P28-2 (3.0 mmol) was dissolved in a solution (160 mL) of $THF/CH_3OH$ (=3:1), NaOH (5.0 mmol) was added, and under a nitrogen atmosphere, the mixture was refluxed to react for 6 h. Then the reaction solution was cooled to room temperature, the solvent was removed by distillation under reduced pressure, and the remaining solid was dissolved in 150 mL of water, then added to HCl solution (6M, 18 mL) to be acidified, and then filtered to obtain a white solid. After vacuum drying, the solid was dissolved in 15 mL of acetic anhydride, refluxed for 6 h, and then cooled to room temperature, and the solvent was removed by distillation under reduced pressure to obtain an intermediate P28-3.

The product P28-3 was analyzed with matrix-assisted laser desorption ionization time-of-flight mass spectrometry (MALDI-TOF MS (m/z): $C_{26}H_{14}BrNO_3$, calculated 467.0, measured 467.3.

(3) The intermediate product P28-3 (1.5 mmol) and potassium acetate (4.0 mmol) were mixed with dry 1,4-dioxane (20 mL), $Pd(dppf)Cl_2$ (0.1 mmol) and bis(pinacolato)diboron (5.0 mmol) and stirred for 48 h at 90° C. under a nitrogen atmosphere. The obtained intermediate was cooled to room temperature, added to water, and then filtered through a pad of diatomite. The filtrate was extracted with dichloromethane, then washed with water, and dried over anhydrous magnesium sulfate. After filtration and evaporation, the crude product was purified with silica gel column chromatography to obtain the intermediate product P28-4.

The product P28-4 was analyzed with matrix-assisted laser desorption ionization time-of-flight mass spectrometry (MALDI-TOF MS (m/z): $C_{32}H_{26}BNO_5$, calculated 515.2, measured 515.3.

(4) P28-4 (2.0 mmol), P25-6 (2.0 mmol) and $Pd(PPh_3)_4$ (0.2 mmol) were added to a mixture of toluene (30 mL)/ethanol (20 mL), potassium carbonate (24 mmol) and water (20 mL), and refluxed for reaction for 12 h under a nitrogen atmosphere. The obtained mixture was cooled to room temperature, added to water, and then filtered through a pad of diatomite, and the filtrate was extracted with dichloromethane, then washed with water, and dried over anhydrous magnesium sulfate. After filtration and evaporation, the crude product was purified with silica gel column chromatography to obtain the final product P28-5.

The product P28-5 was analyzed with matrix-assisted laser desorption ionization time-of-flight mass spectrometry (MALDI-TOF MS (m/z): $C_{41}H_{24}N_4O_3$, calculated 620.2, measured 620.3.

(5) The intermediate P28-5 (2.0 mmol), aniline (2.4 mmol), DMAP (0.04 mmol) and $Et_3N$ (6.0 mmol) were added to dry DCM (20 mL), and the mixture reacted under nitrogen atmosphere at room temperature for 12 h. Then HCl solution (2 mmol/L) was added, and then the mixed solution was extracted with DCM, washed with water, and dried over anhydrous sodium sulfate. After filtration and evaporation, 20 mL of acetic anhydride was added and the mixture was refluxed under stirring for 6 h. After cooling to room temperature, the solvent was removed by distillation under reduced pressure, and the crude product was purified by silica gel column chromatography to obtain Compound P28.

The product P28 was analyzed with matrix-assisted laser desorption ionization time-of-flight mass spectrometry (MALDI-TOF MS (m/z): $C_{47}H_{29}N_5O_2$, calculated 695.2, measured 695.0.

Elemental analysis: theoretical: C, 81.13; H, 4.20; N, 10.07; measured C, 81.14; H, 4.21; N, 10.06.

Example 5

Synthesis of Compound P32, with the following synthesis scheme:

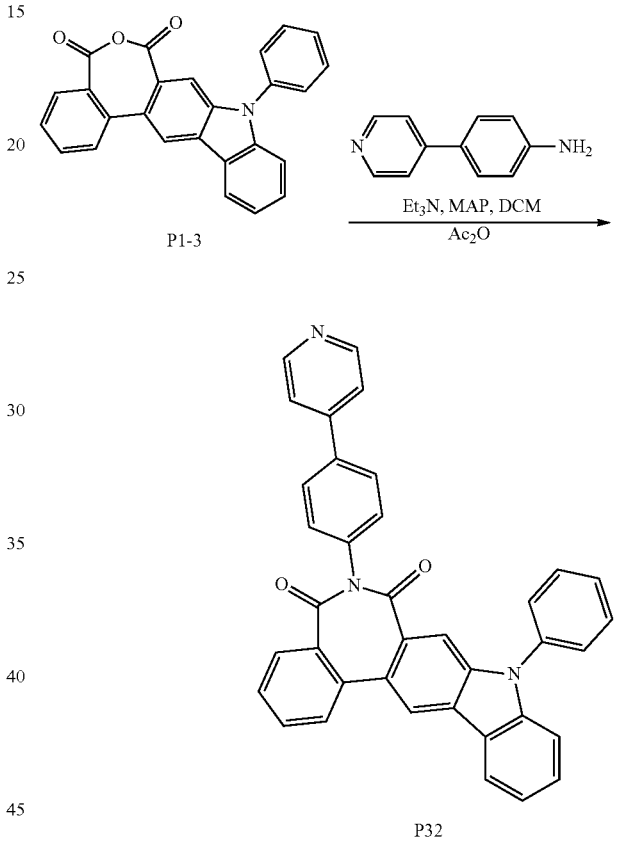

(1) Intermediate P1-3 (2.0 mmol), 4-pyridinyl aniline (2.4 mmol), DMAP (0.04 mmol) and $Et_3N$ (6.0 mmol) were added to dry DCM (20 mL), and the mixture reacted under nitrogen atmosphere at room temperature for 12 h. Then HCl solution (2 mmol/L) was added, and then the mixed solution was extracted with DCM, washed with water, and dried over anhydrous sodium sulfate. After filtration and evaporation, 20 mL of acetic anhydride and the mixture was refluxed under stirring for 6 h. After cooling to room temperature, the solvent was removed by distillation under reduced pressure, and the crude product was purified by silica gel column chromatography to obtain Compound P32.

The product P32 was analyzed with matrix-assisted laser desorption ionization time-of-flight mass spectrometry (MALDI-TOF MS (m/z): $C_{37}H_{23}N_3O_2$, calculated 541.2, measured 541.0.

Elemental analysis: theoretical: C, 82.05; H, 4.28; N, 7.76; measured C, 82.04; H, 4.27; N, 7.76.

Example 6

Synthesis of Compound P133, with the following synthesis scheme:

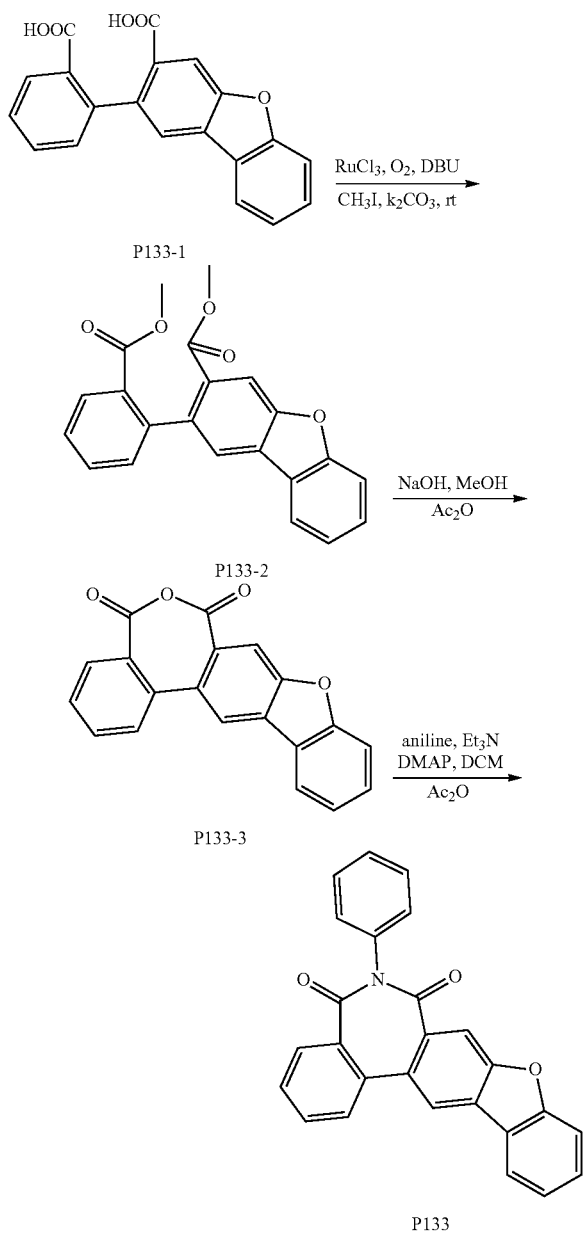

The specific synthesis includes the following steps:

(1) Compound P133-1 (10.0 mmol), RuCl$_3$ (1.0 mmol), and DBU (10.0 mmol) were dissolved in DME (25 mL), and reacted at 110° C. for 30 h in an oxygen environment. After cooling to room temperature, iodomethane (50.0 mmol) and K$_2$CO$_3$ (50.0 mmol) were added and stirred for reaction for 6 h at room temperature. After the reaction was finished, the mixture was extracted with ethyl acetate, then washed with 50 mL of water three times, and dried over anhydrous magnesium sulfate. After filtration and evaporation, the organic phase was evaporated by rotary evaporation to remove solvent. The crude product was purified with silica gel column chromatography using an eluent of ethyl acetate/petroleum ether (1:5, volume ratio), to obtain a solid product P133-2.

The product P133-2 was analyzed with matrix-assisted laser desorption ionization time-of-flight mass spectrometry (MALDI-TOF MS (m/z): C$_{22}$H$_{16}$O$_5$, calculated 360.1, measured 360.0.

(2) The intermediate P133-2 (3.0 mmol) was dissolved in a solution (160 mL) of THF/CH$_3$OH (=3:1), NaOH (5.0 mmol) was added, and under a nitrogen atmosphere, the mixture was refluxed to react for 6 h. Then the reaction solution was cooled to room temperature, the solvent was removed by distillation under reduced pressure, and the remaining solid was dissolved in 150 mL of water, and then added to HCl solution (6M, 18 mL) to be acidified, and then filtered to obtain a white solid. After vacuum drying, the solid was dissolved in 15 mL of acetic anhydride, refluxed for 6 h, and then cooled to room temperature, and the solvent was removed by distillation under reduced pressure to obtain an intermediate P133-3.

The product P133-3 was analyzed with matrix-assisted laser desorption ionization time-of-flight mass spectrometry (MALDI-TOF MS (m/z): C$_{20}$H$_{10}$O$_4$, calculated 314.1, measured 314.3.

(3) The intermediate P133-3 (2.0 mmol), aniline (2.4 mmol), DMAP (0.04 mmol) and Et$_3$N (6.0 mmol) were added to dry DCM (20 mL), and the mixture reacted under nitrogen atmosphere at room temperature for 12 h. Then HCl solution (2 mmol/L) was added, and then the mixed solution was extracted with DCM, washed with water, and dried over anhydrous sodium sulfate. After filtration and evaporation, 20 mL of acetic anhydride was added and the mixture was refluxed under stirring for 6 h. After cooling to room temperature, the solvent was removed by distillation under reduced pressure, and the crude product was purified by silica gel column chromatography to obtain Compound P133.

The product P133 was analyzed with matrix-assisted laser desorption ionization time-of-flight mass spectrometry (MALDI-TOF MS (m/z): C$_{26}$H$_{15}$NO$_3$, calculated 389.1, measured 389.1.

Elemental analysis: theoretical: C, 80.19; H, 3.88; N, 3.60; measured C, 80.18; H, 3.89; N, 3.61.

With respect to Compounds in TABLE 1, the distribution of the molecular frontier orbitals was optimized and calculated by applying a density functional theory (DFT) and using a Gaussian 09 software package with B3LYP/6-31G (d) calculation level. Meanwhile, based on time-dependent density functional theory (TD-DFT), LUMO energy level, HOMO energy level, singlet energy level T1 and triplet energy level T1 of the molecules were simulated and calculated. Test results are shown in Table 1.

TABLE 1

Energy levels of compounds

| Compound | HOMO (eV) | LUMO (eV) | $S_T$ (eV) | $E_T$ (eV) |
|---|---|---|---|---|
| P1 | −5.68 | −1.45 | 3.65 | 2.91 |
| P2 | −5.67 | −1.60 | 3.55 | 2.78 |
| P10 | −5.61 | −1.46 | 3.61 | 2.79 |
| P19 | −5.59 | −1.43 | 3.62 | 2.78 |
| P25 | −5.71 | −1.76 | 3.60 | 2.90 |
| P28 | −5.67 | −2.20 | 3.06 | 2.78 |
| P32 | −5.69 | −1.65 | 3.55 | 2.90 |
| P36 | −5.56 | −1.47 | 3.62 | 2.74 |
| P70 | −5.59 | −1.67 | 3.56 | 2.93 |

TABLE 1-continued

Energy levels of compounds

| Compound | HOMO (eV) | LUMO (eV) | $S_T$ (eV) | $E_T$ (eV) |
|---|---|---|---|---|
| P81 | −5.69 | −1.69 | 3.55 | 2.96 |
| P133 | −5.68 | −1.66 | 4.03 | 2.92 |
| P178 | −5.68 | −1.66 | 4.03 | 2.92 |
| HT-Ref. | −5.34 | −1.25 | 3.05 | 2.71 |
| Host-Ref. | −5.41 | −1.76 | 2.67 | 2.65 |

It can be seen from Table 1 that the compounds according to the present disclosure exhibited suitable HOMO and LUMO energy levels and an extremely high triplet energy level $E_T$. Therefore, the energy transfer between the host material and the guest material can be effectively realized without the risk of back transferring of charges.

Device Example 1

This example provides an organic light-emitting device, as shown in FIG. 1. The OLED device includes a substrate 1, an ITO anode 2, a first hole transport layer 3, a second hole transport layer 4, an electron blocking layer 5, a light-emitting layer 6, a first electron transport layer 7, a second electron transport layer 8, a cathode 9 (magnesium silver electrode) and a capping layer 10. The ITO anode 2 has a thickness of 10 nm, the first hole transport layer 3 has a thickness of 10 nm, the second hole transport layer 4 has a thickness of 95 nm, the electron blocking layer has a thickness of 30 nm, the light-emitting layer 6 has a thickness of 30 nm, the first electron transport layer 7 has a thickness of 30 nm, the second electron transport layer 8 has a thickness of 5 nm, the magnesium silver electrode 9 has a thickness of 15 nm, and the capping layer has a thickness of 100 nm.

The OLED device was manufactured by the following steps.

1) A glass substrate 1 was cut into a size of 50 mm×50 mm×0.7 mm, ultrasonically treated respectively in isopropanol and deionized water for 30 min, and then exposed to ozone for cleaning for 10 min; and the obtained glass substrate with an ITO anode layer 2 was mounted on a vacuum deposition apparatus.

2) Under a vacuum degree of 2×10⁻⁶ Pa, a hole transport material HT1: HAT-CN was vacuum-evaporated onto the ITO anode 2 to form a first hole transport layer 3 having a thickness of 10 nm, where a mass ratio of HT1 to HAT-CN was 98:2.

3) Compound P1 according to the present disclosure was vacuum-evaporated on the first hole transport layer 3 to form a second hole transport layer 4 having a thickness of 95 nm.

4) An electron blocking material Prime-1 was vacuum-evaporated on the second hole transport layer 4 to form the electron blocking layer 5 having a thickness of 30 nm.

5) A host material BH and a guest material BD-1 were co-deposited on the electron blocking layer 5 to form the light-emitting layer 6 with a thickness of 30 nm, where a mass ratio of BH to BD-1 was 97:3.

6) A first electron transport material ET-1 was vacuum-evaporated on the light-emitting layer 6 to form a first electron transport layer 7 having a thickness of 30 nm.

7) A second electron transport material LiF was vacuum-evaporated on the first electron transport layer 7 to form a second electron transport layer 8 having a thickness of 5 nm.

8) Magnesium-silver was vacuum-evaporated on the second electron transport layer 8 to form a cathode 9 having a thickness of 15 nm, where a mass ratio of Mg to Ag was 9:1.

9) A hole material CPL-1 having a high refractive index was vacuum-evaporated on the cathode 9 to form a cathode capping layer 10, referred as a capping layer (CPL), having a thickness of 100 nm.

The structures of the compounds used in the present examples are as follows:

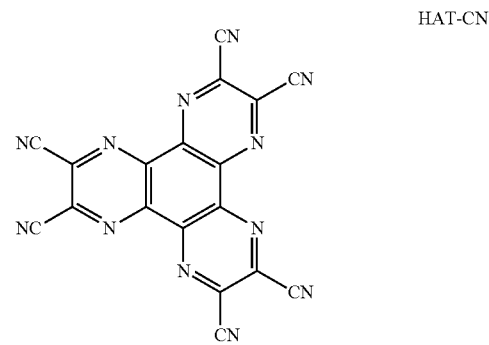

HAT-CN

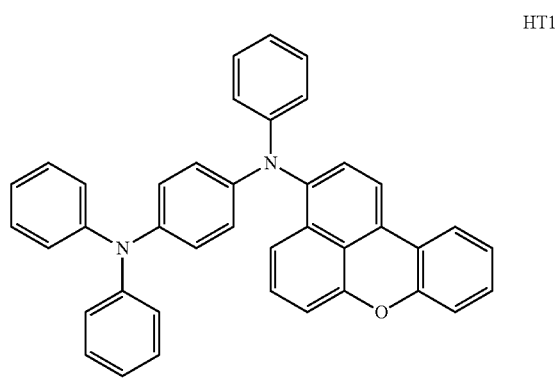

HT1

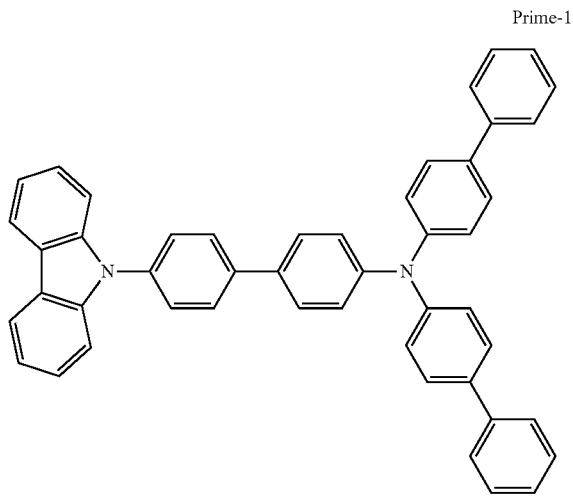

Prime-1

Compound BH

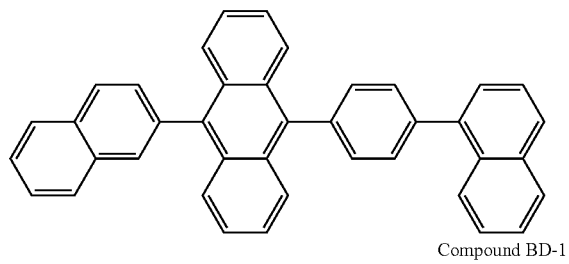

Compound BD-1

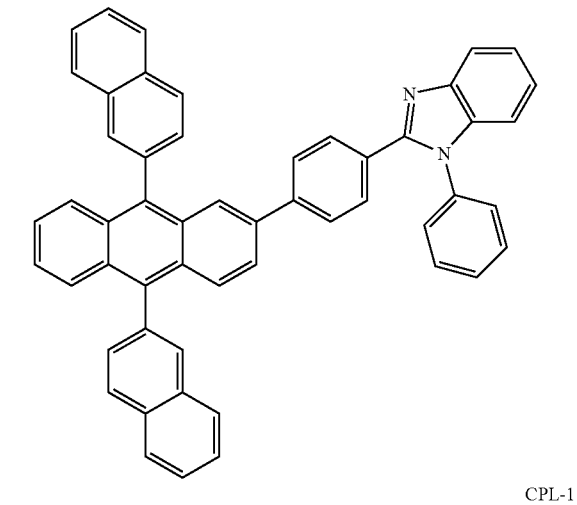

ET-1

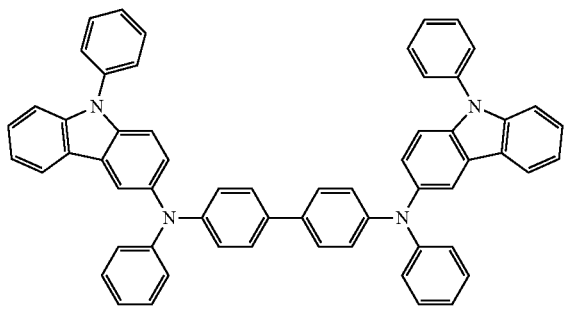

CPL-1

Device Example 2

This example differs from Device Example 1 in that Compound P2 according to the present disclosure was used as the material of the hole transport layer.

Device Example 3

This example differs from Device Example 1 in that Compound P10 according to the present disclosure was used as the material of the hole transport layer.

Device Example 4

This example differs from Device Example 1 in that Compound P19 according to the present disclosure was used as the material of the hole transport layer.

Device Example 5

This example differs from Device Example 1 in that Compound P25 according to the present disclosure was used as the host material of the light-emitting layer.

Device Example 6

This example differs from Device Example 1 in that Compound P28 according to the present disclosure was used as the host material of the light-emitting layer.

Device Example 7

This example differs from Device Example 1 in that Compound P32 according to the present disclosure was used as the host material of the light-emitting layer.

Device Example 8

This example differs from Device Example 1 in that Compound P36 according to the present disclosure was used as the material of the hole transport layer.

Device Example 9

This example differs from Device Example 1 in that Compound P70 according to the present disclosure was used as the host material of the light-emitting layer.

Device Example 10

This example differs from Device Example 1 in that Compound P81 according to the present disclosure was used as the host material of the light-emitting layer.

Device Example 11

This example differs from Device Example 1 in that Compound P133 according to the present disclosure was used as the host material of the light-emitting layer.

Device Example 12

This example differs from Device Example 1 in that Compound P178 according to the present disclosure was used as the host material of the light-emitting layer.

Device Comparative Example 1

This comparative example differs from Device Example 1 in that Compound HT-Ref. shown below was used as the material of the hole transport layer.

HT-Ref

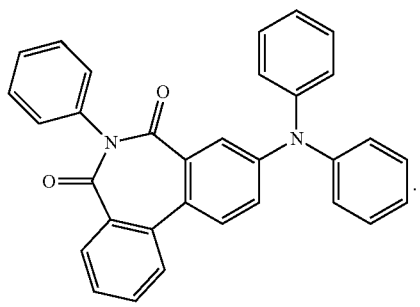

Device Comparative Example 2

This comparative example differs from Device Example 1 in that Compound Host-Ref. shown below was used as the host material of the light-emitting layer.

Host-Ref

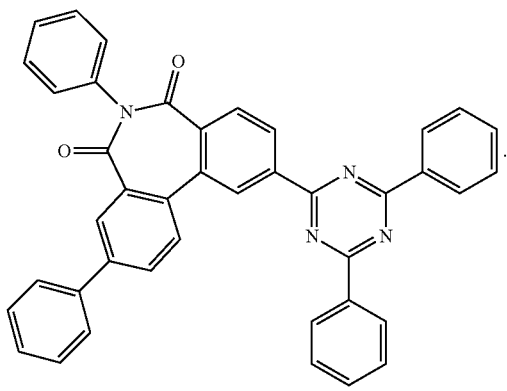

A Keithley 2365A digital nanovoltmeter was used to measure the currents of the organic light-emitting devices manufactured according to the examples and comparative examples at different voltages. The currents were divided by the light-emitting area to calculate current densities of the organic light-emitting device at different voltages. Konicaminolta CS-2000 spectroradiometer was used to measure the brightness and the radiant energy flux density of the organic light-emitting devices prepared in the examples and comparative examples at different voltages. According to the current densities and brightness of the organic light-emitting devices at different voltages, a current efficiency (CE, CdA$^{-1}$) under the same current density (10 mA/cm$^2$) was obtained. In the obtained current-voltage-brightness curve, a voltage corresponding to 10 mA/cm$^2$ was a driving voltage $V_{on}$. The service life LT95 was obtained by measuring a lasting time period before the brightness of the organic light-emitting device was reduced to 95% of an initial brightness (measured at 50 mA/cm$^2$). Test results are listed in Table 2.

TABLE 2

Results of the light-emitting performance test of the devices

| No. | Material | Driving Voltage (V) | CE (10 mA/cm$^2$) (cd A$^{-1}$) | Service Life LT95 (h) |
|---|---|---|---|---|
| Device Example 1 | P1 | 3.71 | 5.3 | 69 |
| Device Example 2 | P2 | 3.75 | 5.1 | 67 |
| Device Example 3 | P10 | 3.70 | 6.1 | 70 |
| Device Example 4 | P19 | 3.69 | 6.0 | 71 |
| Device Example 5 | P25 | 3.81 | 5.5 | 70 |
| Device Example 6 | P28 | 3.78 | 5.6 | 70 |
| Device Example 7 | P32 | 3.82 | 5.4 | 69 |
| Device Example 8 | P36 | 3.74 | 4.9 | 68 |
| Device Example 9 | P70 | 3.83 | 5.5 | 67 |
| Device Example 10 | P81 | 3.83 | 5.3 | 66 |
| Device Example 11 | P133 | 3.79 | 5.4 | 69 |
| Device Example 12 | P178 | 3.81 | 5.3 | 70 |
| Device Comparative Example 1 | HT-Ref. | 4.13 | 4.0 | 53 |
| Device Comparative Example 2 | Host-Ref. | 4.01 | 4.6 | 60 |

As revealed by the data in Table 2, when the compounds provided by the present disclosure are used as the materials of the hole transport layer and the host material of the light-emitting layer of the organic electroluminescent device, a luminous efficiency of the device is enhanced, the driving voltage is lowered, and the service life is prolonged. The current efficiency of the organic light-emitting devices using the compounds of the present disclosure can reach 4.9 cdA$^{-1}$ or more, the driving voltage is lower than 3.83 V, and the service life LT95 is 67 h or longer. These performances are significantly better than comparative device 1 and comparative device 2.

Another aspect of the present disclosure further provides a display apparatus, which includes a display panel, and the display panel includes the organic light-emitting device as described above.

Figure 3:
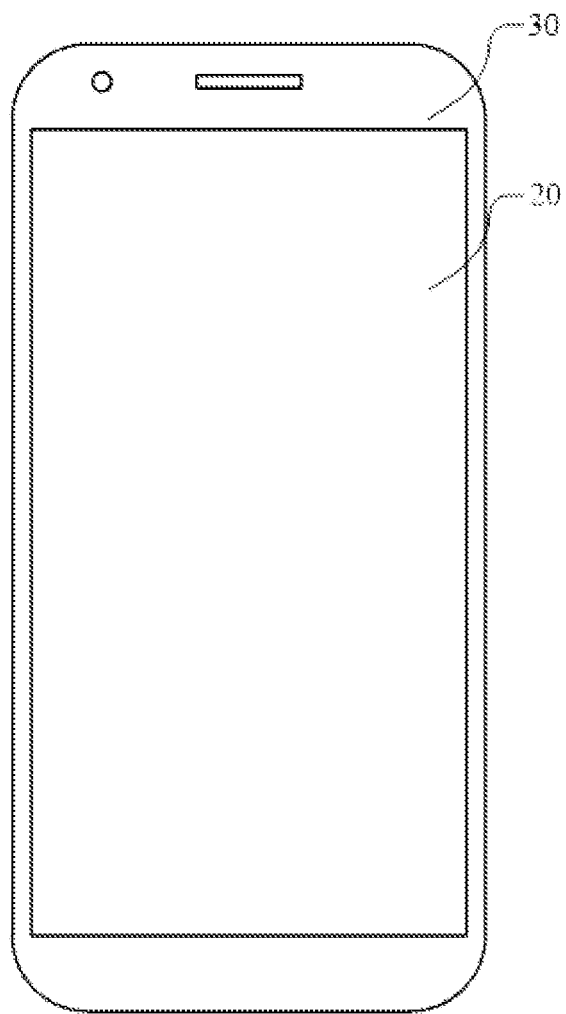
FIG. 3 is a schematic diagram of a display apparatus according to an embodiment of the present disclosure.

In the present disclosure, the organic light-emitting device can be OLED, which is applicable to the organic light-emitting display apparatus. The display apparatus can be a display screen of a mobile phone, a computer, a TV, a smart watch, a smart car, a VR or AR helmet, or any other smart devices. FIG. 3 is a schematic diagram of a display apparatus according to an embodiment of the present disclosure. In FIG. 3, 20 indicates a display panel of a mobile phone, and 30 indicates a display apparatus.

The above are preferred embodiments for illustrating the present disclosure, but not intended to limit the present disclosure. Any changes, equivalent substitutions, or improvements made within the principles of the present disclosure shall fall in the protection scope of the present disclosure.

What is claimed is:

1. A compound consisting of any one of the following compounds P1, P10, P25, P28, P32 or P133:

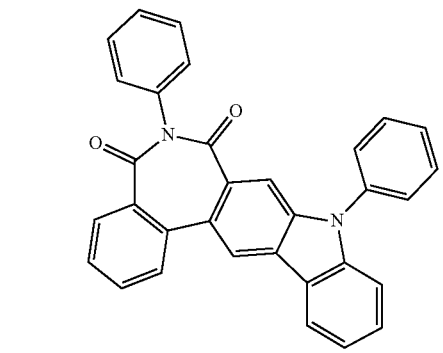
P1

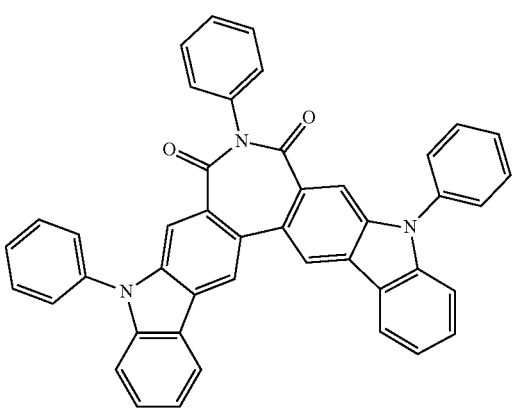
P10

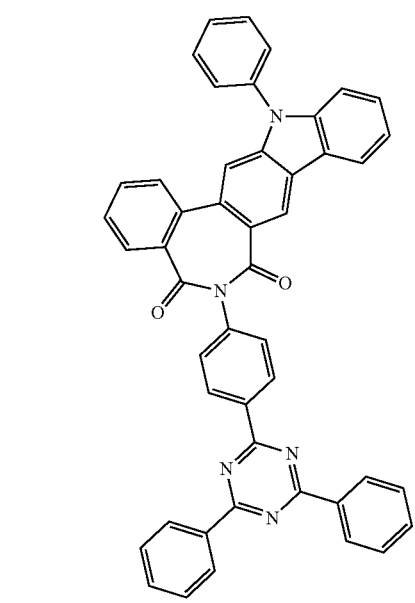
P25

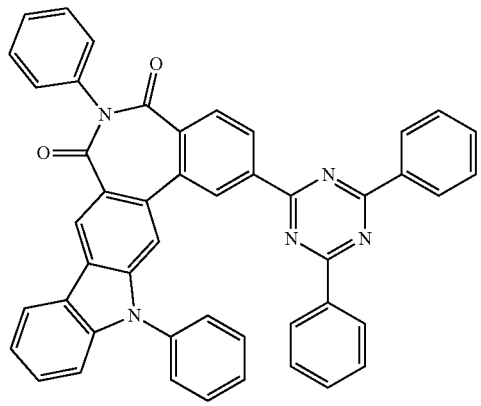
P28

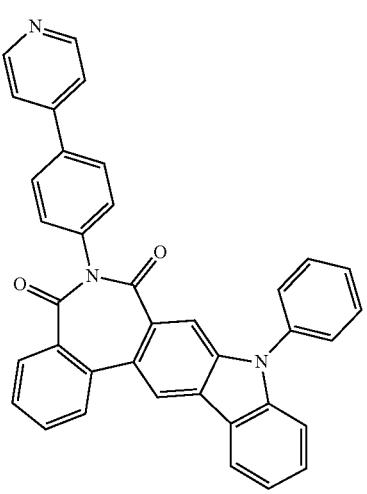
P32

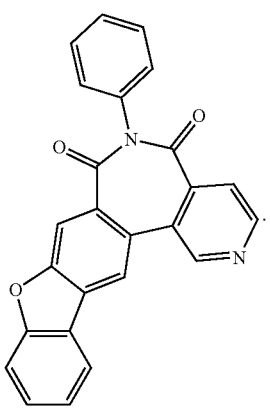
P133

2. The compound according to claim 1, having a triple energy level $E_T$ greater than or equal to 2.6 eV.

3. The compound according to claim 1, having a glass transition temperature Tg greater than or equal to 120° C.

4. A display panel, comprising an organic light-emitting device,
wherein the organic light-emitting display device comprises:
an anode;
a cathode arranged oppositely to the anode; and
a light-emitting layer disposed between the anode and the cathode, wherein the light-emitting layer comprises a host material and a guest material, and the host material of the light-emitting layer comprises a compound according to claim 1.

5. The display panel according to claim 4, wherein the organic light-emitting device further comprises a hole transport layer.

6. The display panel according to claim 4, wherein the organic light-emitting device further comprises a hole injection layer.

7. A display apparatus, comprising the display panel according to claim 4.

* * * * *